(12) United States Patent
Rurack et al.

(10) Patent No.: US 12,188,930 B2
(45) Date of Patent: Jan. 7, 2025

(54) LABEL-FREE OPTICAL DETECTION IN CAPTURE ZONES IMMOBILIZED ON STRIPS FOR LATERAL FLOW ASSAYS

(71) Applicant: Bundesrepublik Deutschland, vertreten durch die Bundesministerin für Wirtschaft und Energie, Berlin (DE)

(72) Inventors: Knut Rurack, Berlin (DE); Estela Climent, Berlin (DE); Wei Wan, Berlin (DE)

(73) Assignee: Bundesrepublik Deutschland, vertreten durch die Bundesministerin für Wirtschaft und Energie, Berlin (DE)

(*) Notice: Subject to any disclaimer, the term of this patent is extended or adjusted under 35 U.S.C. 154(b) by 670 days.

(21) Appl. No.: 16/771,413

(22) PCT Filed: Dec. 3, 2018

(86) PCT No.: PCT/EP2018/083359
§ 371 (c)(1),
(2) Date: Jun. 10, 2020

(87) PCT Pub. No.: WO2019/115273
PCT Pub. Date: Jun. 20, 2019

(65) Prior Publication Data
US 2020/0340989 A1 Oct. 29, 2020

(30) Foreign Application Priority Data
Dec. 11, 2017 (DE) .................. 10 2017 129 476.7

(51) Int. Cl.
*G01N 33/543* (2006.01)
*G01N 21/77* (2006.01)
*G01N 21/84* (2006.01)

(52) U.S. Cl.
CPC ....... *G01N 33/54388* (2021.08); *G01N 21/77* (2013.01); *G01N 21/8483* (2013.01); *G01N 2021/7786* (2013.01)

(58) Field of Classification Search
CPC ........... G01N 33/53; G01N 2021/7786; G01N 2021/752; G01N 2021/754; G01N 2021/757; G01N 2458/00; G01N 21/77; G01N 21/8483; G01N 21/85; G01N 2021/8557; G01N 2021/869; G01N 2600/00; G01N 33/558; G01N 2458/40; G01N 33/54387; G01N 33/54388; G01N 33/54389; G01N 33/54386; G01N 33/543; B01L 2300/0825
USPC .......... 435/7.1, 287.7, 287.9, 970, 805, 810; 422/400, 401, 420, 421, 425, 426, 430; 436/169, 170, 514, 518, 530, 810
See application file for complete search history.

(56) References Cited

U.S. PATENT DOCUMENTS

| | | | | |
|---|---|---|---|---|
| 2015/0241425 A1* | 8/2015 | McKee | ............... | G01N 33/558 |
| | | | | 422/69 |
| 2016/0299136 A1 | 10/2016 | Ozalp et al. | | |
| 2020/0124597 A1* | 4/2020 | Climent Terol | ..... | G01N 33/582 |

FOREIGN PATENT DOCUMENTS

| | | | | |
|---|---|---|---|---|
| CN | 105339795 A | 2/2016 | | |
| CN | 106932391 A | 7/2017 | | |
| WO | 2008007359 A1 | 1/2008 | | |
| WO | WO-2008007359 A2 * | 1/2008 | ......... | G01N 33/5302 |
| WO | 2013105090 A1 | 7/2013 | | |
| WO | WO-2015088455 A1 * | 6/2015 | ........... | C12N 15/111 |
| WO | 2018172278 A1 | 9/2018 | | |

OTHER PUBLICATIONS

Climent, E., Gröninger, D., (2013), Selective, Sensitive, and Rapid Analysis with Lateral-Flow Assays Based on Antibody-Gated Dye-Delivery Systems: The Example of Triacetone Triperoxide. Chem. Eur. J., 19 (Year: 2013).*
Madru et al. ("Novel extraction supports based on immobilised aptamers: Evaluation for the selective extraction of cocaine" Talanta 85 (2011) 616-624). (Year: 2011).*
Korean allowance of patent for application No. 10-2020-7020119 dated Apr. 11, 2022.
Australian examination report for patent application No. 2018382349 dated Dec. 15, 2021.
Climent et al., "Selective, Sensitive, and Rapid Analysis with Lateral-Flow Assays Based on Antibody-Gated Dye-Delivery Systems: The Example of Triacetone Triperoxide", Chemistry A European Journal, (2013), 19, pp. 4117-4122.
Korean office action for patent application No. 10-2020-7020119 dated Sep. 5, 2021.
German office action for patent application No. 10 2017 129 476.7 dated Nov. 8, 2021.
Climent et al., "Selective, Sensitive, and Rapid Analysis with Lateral-Flow Assays Based on Antibody-Gated Dye-Delivery Systems: The Example of Triacetone Triperoxide", Chemistry A European Journal, (2013), vol. 19, pp. 4117-4122.
Vasapollo et al. "Molecularly Imprinted Polymers: Present and Future Prospective", International Journal of Molecular Sciences, (2011), vol. 12, pp. 5908-5945.
International search report for patent application No. PCT/EP2018/083359 dated Jan. 31, 2019.

(Continued)

*Primary Examiner* — Gary Counts
(74) *Attorney, Agent, or Firm* — Bachman & LaPointe, P.C.

(57) ABSTRACT

A test strip comprising a porous matrix, the test strip includes a sample application zone for applying a liquid sample including an analyte; a reporter release zone, having a sensing material, the sensing material being adapted to selectively interact with the analyte by releasing an optical reporter, the reporter release zone being arranged downstream of the sample application zone; and a detection zone, having a capture material, the capture material being adapted to selectively bind the optical reporter and being arranged downstream of the reporter release zone.

17 Claims, 8 Drawing Sheets

(56) References Cited

OTHER PUBLICATIONS

Indian office action for patent application No. 202017026424 dated Jan. 28, 2021.
Chinese Office Action dated Jan. 28, 2023 for corresponding application 201880079918.6.

* cited by examiner

LABEL-FREE OPTICAL DETECTION IN CAPTURE ZONES IMMOBILIZED ON STRIPS FOR LATERAL FLOW ASSAYS

FIELD AND BACKGROUND

The present invention relates to methods for the rapid and sensitive detection of analytes, e.g. in medical diagnostics and environmental monitoring, in the area of security, occupational health and safety as well as in food related sectors. In case that the analyte is a certain nucleic acid, its detection is also crucial in forensics or in microbiology-related issues such as bacterial or other microbial contamination. In particular, the present invention relates to lateral flow assay formats.

Among all of the methods employed for rapid tests, lateral flow assays are the most commonly used, and hundreds of test kits based on this technique are available on the market. This type of assay comprises usually a membrane strip, often nitrocellulose or glass fibres, in which the sample-indicator complex can be transported through the capillary force of the liquid within the porous structure of the strip. This membrane strip usually comprises a sample application zone and a detection zone, in which a capturing reagent (often an antibody or an antibody fragment) for the analyte is immobilized. Finally, an absorbing pad at the end of the strip usually ensures a continuous capillary flow of the liquid.

However, a major drawback of known lateral flow assays is that most of the capture agents either indicate the analyte only indirectly through competition with a labelled analogue, or follow the traditional indicator approach, i.e. have to accomplish selective and sensitive binding as well as generating an intense signal at the same time. Such is often difficult to achieve and in most cases, reduces the sensitivity considerably. Another drawback of known lateral flow assays is that only a few analytes can be measured per assay. Furthermore, in most cases a second binding agent able to bind directly or indirectly to the analyte is necessary, e.g. a secondary labelled antibody or antibody fragment.

Known methods are mainly based on the traditional indicator approach, in which the interaction between the analyte and the indicator or immunoreagent has to follow defined stoichiometries and the binding and the indication event are intrinsically coupled. In many cases, the detection is only accomplished after using a second binding agent, which not only increases the costs, but introduces potentially more errors.

BRIEF SUMMARY

Against this background, according to a first embodiment, a test strip comprising a porous matrix is proposed. The test strip comprises:
- a sample application zone for applying a liquid sample comprising an analyte, wherein the analyte is typically dissolved or solubilized in a liquid;
- a reporter release zone, comprising a sensing material, the sensing material being adapted to selectively interact with the analyte by releasing an optical reporter in response to the presence of the analyte, the reporter release zone being arranged downstream of the sample application zone;
- a detection zone, comprising a capture material, the capture material being adapted to selectively bind the optical reporter and being arranged downstream of the reporter release zone.

In other words, the reporter is released from the sensing material on the test strip if a liquid containing the analyte wets the sensing material. Since the test strip comprises a porous matrix, a liquid (e.g. a solvent) driven by capillary forces can flow within the porous matrix and subsequently wet all zones. The released reporter is transported by a liquid stream, typically by a solvent flow (stream), to the detection zone. With respect to the liquid flow or stream, the reporter release zone is located downstream in comparison to the sample application zone. Further, the detection zone, with respect to the liquid flow or stream is located downstream in comparison to the reporter release zone. As to the sequence of the different zones, the sample application zone is the first, the reporter release zone is the second, and the detection zone is the third zone with or in the direction of a continuous or discontinuous current of the streaming liquid. The presence and/or an amount of the reporter in at least one detection zone is/are typically quantified by detection means. However, the presence and apparent amount of the analyte can also occasionally be evaluated by a mere visual inspection using a suitable illumination of the detection zone without any further equipment.

According to another embodiment a method for detecting an analyte is proposed. The method comprises:
- providing a test strip encompassing a porous matrix, the test strip comprising at least a sample application zone; a reporter release zone, comprising a sensing material, wherein the sensing material is adapted to selectively interact with the analyte by releasing a reporter after being in contact with the analyte; and a detection zone, comprising a capture material, wherein the capture material is adapted to selectively bind the reporter;
- applying a sample to the sample application zone;
- detecting a presence and/or a quantity and/or a concentration of the reporter in the at least one detection zone;
- determining a presence and/or a concentration of the analyte in the sample.

According to an embodiment, the above method comprises a continuous or discontinuous fluid stream from the sample application zone to the reporter release zone and from the reporter release zone to at least one detection zone.

BRIEF DESCRIPTION OF THE DRAWINGS

A full and enabling disclosure of the present invention, including the best mode thereof, to one of ordinary skill in the art, is set forth more particularly in the remainder of the description, including reference to the accompanying figures.

Figure 1:
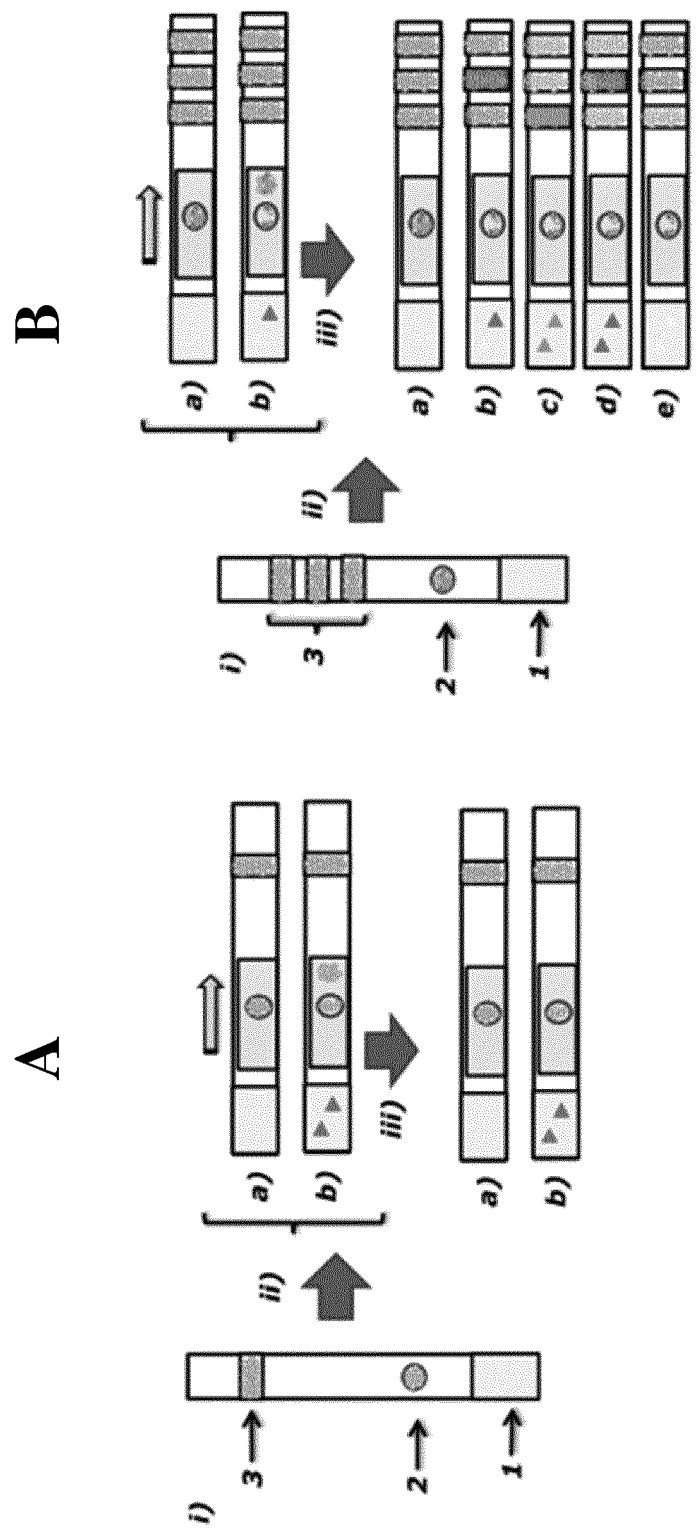
FIG. 1 shows the working principle of the test strip or dip stick adapted for a lateral flow assay for the detection of a single analyte (FIG. 1A) and 3 analytes (FIG. 1B). i) shows the respective strip before flowing ii) during the flow in absence (a) and in presence (b-e) of the analytes and iii) after the flow.

In the following detailed description, reference is made to the accompanying figures, which form a part hereof, and in which are shown by way of illustration specific embodiments and features of the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

DETAILED DESCRIPTION

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification (above and below) and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or openended and do not exclude additional, unrecited elements or method steps.

As used in this specification (above and below) and claims, the term "porous matrix" is to be understood as comprising typically an irregular structure comprising an open-porous solid material which is typically inert and stable in solvents, e.g. buffer solutions.

As used in this specification (above and below) and claims, the term "mesoporous inorganic material" is to be understood as encompassing typically a solid body comprising mesopores. Mesopores have an average pore diameter of between 2 nm and 50 nm. A well-established method to measure the average pore diameter of these inorganic materials is nitrogen sorption porosimetry, electron microscopy, e.g. scanning electron microscopy or transmission electron microscopy.

As used in this specification (above and below) and claims, the term "mesoporous sensing material" comprises an inorganic mesoporous material which is commercially available or laboratory-made and selected, e.g., from materials known as MCM-41, HMS, MSU-n, MSU-V, FSM-16, KSW-2, SBA-n (n=1, 2, 3, 8, 11-16), FDU-n (12, 14, 15, 16), UVM-7, UVM-8, M-UVM-7 or M-UVM-8, A1203-type MCM-41. Typically, the inorganic mesoporous material comprises silica, i.e. $SiO_2$ or alumina, i.e. $Al_2O_3$. Mesoporous inorganic materials may also comprise $TiO_2$, carbon, carbonitride, silicon carbide, silicon oxycarbide, silicon carbonitride, silicon nitride, silicon oxynitride, silicon aluminium nitride, or silicoboron carbonitride. The mesopores of said inorganic material contain a reporter. The release of said reporter from said mesopores is blocked by a pore closing material. The pore closing material may be chemically functionalized, i.e. provided with functional groups, such as, e.g., amino groups or carboxyl groups. The modification of inorganic materials by small organic molecules carrying such functional groups is well known and therefore does not need to be specified further.

As used in this specification (above and below) and claims the term "sample" is to be understood as a liquid containing the analyte in an unknown concentration. Typically, the analyte is present in the sample in dissolved form. In such a case, the sample comprises a solute as well. The solute contained in the sample may be used as the liquid phase which generates a fluid connection between the sample application zone and the reporter release zone. In addition to the solute contained in the sample, pure solvent can be applied to the sample application zone after the sample has been applied. This solvent may be used to generate or to maintain a fluid connection between the reporter release zone and the detection zone. However, the sample may also be dried at the sample application zone. In such a case, a pure solvent of the same type or of another type may be applied to the sample application zone in order to generate a fluid connection with the reporter release zone. Finally, a fluid connection is generated between the reporter release zone and the detection zone.

As used in this specification (above and below) and claims, the term "reporter" is used synonymously with the term "indicator". It comprises an entity which can be entrapped within pores of a mesoporous material to produce a sensing material as explained above and below. The reporter can be detected either directly (e.g. by its color) or indirectly, e.g., after excitation by its fluorescence, phosphorescence, or luminescence.

As used in this specification (above and below) and claims, the terms "fluorescence measurement", "fluorescent dye", and any related thereto term is to be understood as comprising an optical property or its detection, e.g., an excitation wavelength, an emission wavelength, a fluorescence intensity, a fluorescence quantum yield, a fluorescence life time or decay, and/or a fluorescence ratio, or the like or its detection.

The pore closing material of the sensing material is releasable. In particular, the pore closing material is typically organic and is bound detachable (i.e. non-covalently) to the inorganic mesoporous material. In particular, the pore-closing material is non-covalently bound to the mesoporous material by a compound that is anchored to the porous material. The pore-closing material is selected to specifically bind the analyte. The reporter substance is released from the pores when the pore-closing material binds the analyte. The analyte is typically contained (or not contained) in a liquid sample that wets the reporter reservoir, i.e. the reporter release zone. In other words, all pores at the surface of the mesoporous material are capped, and thus closed, by the pore closing material. Therefore, the reporter which is stored inside the pores cannot be released into a surrounding liquid, as long as the analyte is not specifically bound by the pore-closing material and the pore-closing material is released from the porous inorganic material. If a liquid which contains the analyte comes into contact with the reporter reservoir at the reporter release zone, that allows the non-covalent bonds to be detached and enables specific bond(s) between the pore-closing material and the analyte to be formed and thus prevents re-formation of the non-covalent bond between the pore-closing material and the mesoporous material or any compound anchored thereto. If the wetting liquid does not contain the analyte, the non-covalent bond of the capping material to the inorganic porous material will be strong enough to hold the pore closing material in the proximity of the pore. Therefore, the mesopores are blocked and the reporter is thus substantially prevented from escaping the mesopores and hence, no signal can be generated.

In other words, the pores of the inorganic porous material are closed by an entity which comprises an organic molecule, e.g. a hapten-like substance, which is associated with a pore closing material. The pore closing material is non-covalently bound to an organic molecule (referred to therein as compound) which is tightly fixed at the surface of the mesoporous material. The reporter—which is initially arranged within the pores—is releasable from the pores, by detaching of the pore closing material from the pore openings when the pore-closing material binds a particular analyte—i.e. one assigned to the specific reporter—which is present in a liquid sample. After binding to the analyte, the pore closing material is hindered to rebind to the compound (which is, e.g., a hapten-like substance) which is fixed at the mesoporous material in close proximity to the pores and thus the pore-closing material is detached.

The pore closing material is selected from the group comprising an antibody, an antibody fragment, a receptor protein, an oligonucleotide, and an aptamer. The aptamer may be selected from an oligo-aptamer and a peptide aptamer. The antibody, the receptor protein, the oligonucleotide and the aptamer are able to specifically bind the analyte. Additionally, the pore closing material may comprise an inorganic nanoparticle comprising, e.g., gold, silver or iron oxide; a metal cluster comprising, e.g., gold or silver; a nanocrystal comprising, e.g., cadmium sulfide or another semiconductor material; or a carbon nanodot or a nanodiamond. The mentioned inorganic nanoparticle, metal cluster or nanocrystal has a size up to 50 nm, typically up to 30 nm. According to typical embodiments, its surface is modified by an organic molecule or by an antibody or by an antibody fragment.

The following short description of the basic mechanism of the suggested reporter reservoir, i.e. sensing material, and of the corresponding reporter release system may be given, for example, if the pore closing material comprises an antibody or antibody fragment.

The bond(s) between an antibody and a hapten or the bond(s) between an antibody and a compound (e.g. an organic molecule which resembles a hapten derivative) is(are) non-covalent. Therefore, the pore closing cap (e.g. the antibody) in an appropriate solvent associates and dissociates all the time. The resulting system is dynamic. Since in such dynamic systems the association occurs very fast, whereas the dissociation is rather slow, only insignificant leaching of the reporter from the pores of the reporter reservoir, i.e. from the reporter release zone, occurs. If the reporter reservoir, i.e. the reporter release zone, is dry and not wetted by a solvent, no leaching at all occurs.

Furthermore, the affinity of the analyte towards the antibody is much higher in comparison to the affinity of the hapten (compound) towards the antibody. Therefore, the binding site of the antibody (cap) is effectively blocked in presence of the analyte. Hence, any fast rebinding of the antibody to the hapten (compound) is prevented. Therefore, the antibody may depart from the pore opening sufficiently far while its binding site is blocked.

Therefore, even in the case of a dissociation of the complex between the analyte and the antibody—which comprises a dynamic system as well—no re-sealing of the pore(s) may occur.

As to the mentioned above affinities, the affinity of the antibody towards the analyte is much higher in comparison to the affinity of the antibody towards the hapten as well.

The technical object of the described embodiments is to use several macromolecules or materials immobilized in the detection zone of a lateral flow device with the aim to create a label free and potentially multiplexed detection on lateral flow devices or test strips. These immobilized macromolecules or capture materials are adapted, i.e. selected, to selectively interact with the reporter molecule, i.e. the reporter, which is released from the mesoporous sensing material disposed on or in the sample injection zone, wherein the sensing material is responsible for the specific interaction with the analyte to be detected.

The advantage of the proposed embodiments is that the reporter which is released from the pores of the sensing material is dedicatedly captured only at a well-defined location on the strip, i.e. in the detection zone or in at least one of the detection zones.

In particular, FIG. 1A shows the working principle of a test strip as proposed according to the first embodiment. The test strip i) comprises a sample injection zone, referred to as sample application zone 1, a reporter release zone 2, and a detection zone 3 comprising a capture material able to interact with the optical reporter molecule released from zone 2. During the flow ii) of a solvent along the strip, the optical reporter molecules, i.e. the reporter, which is initially encapsulated in the sensing material that is deposited in the reporter release zone 2 are/is released only when the respective analyte is present in a sample (strip b) and then move with the flow by capillary forces toward the detection zone 3. In the detection zone, the reporter is retained for detection. In the absence of analyte in a sample (strip a), no release is registered, and hence no reporter can be detected in the detection zone. The reporter release zone typically may comprise particles of a mesoporous material filled with reporter molecules, wherein the mesoporous material is able to interact with the analyte by immediately releasing the reporter.

FIG. 1B shows the working principle of test strips according to the first embodiment which are adapted for the detection of multiple analytes. The test strips comprise a sample injection zone 1, a reporter release zone 2 and a detection zone 3. There three different types of sensing material have been deposited on the matrix to form the reporter release zone 2. Said three types of sensing material differ both by the reporter (reporter molecules) which is entrapped inside the mesoporous material and by the analyte-specificity of the corresponding pore closing cap. Thus, the specificity of the pore closing cap is adapted to recognize specifically a given analyte and to release the reporter from the mesopores once the analyte and the cap are bound to each other. As different reporters are assigned to different specificities of the cap, i.e. different analytes, the presence of the corresponding analyte can easily be detected, once the reporter is accumulated in its specific detection zone.

In other words, a mixture of, e.g., three hybrid sensing particles, each containing different reporter molecules and each being able to interact with a different one of three analytes, comprise the reporter release zone 2. In combination therewith, a structured detection zone 3 is provided. In other words, three different detection zones are provided. Each of the three different detection zones comprises a selective capture material, adapted to the specific recognition of one of the three analytes, even in their mixture. During the flow ii), the corresponding optical reporter molecules encapsulated in the sensing materials are released only when the respective analyte is present in the sample (see strips b) to e)) and subsequently "recognized" by the analyte-sensitive cap. The released optical reporter, driven by capillary forces, is carried by the solvent flow in the porous matrix toward the capture zone 3. While the current of the liquid phase (e.g. a solvent) moves towards the end of the strip, the reporter is specifically retained in the designated zone, where it can be detected. In the absence of analyte in a sample (see strip a)), no release of reporter is registered. A continuous current of streaming liquid phase can be supported, e.g. by providing an absorbing pad at the end of the test strip opposite to the sample injection (application) zone.

According to an embodiment a test strip is suggested, wherein the optical reporter is contained in pores of the sensing material, wherein the pores of the sensing material are closed by a pore-closing material, wherein the pore-closing material is selected to specifically bind the analyte, releasing the optical reporter from the pores when the analyte specifically binds to the pore-closing material.

Advantageously, the combination of A): a hybrid nanoparticle material which may release reporter molecules, initially gated in the sample application zone; and B): a specific capture material immobilized in the detection zone, the capture material being adapted to selectively interact with the reporter molecules released from the gated hybrid nanoparticles, is a powerful tool for the design of novel lateral flow devices: On one hand, the gated sensor material is able to produce a massive signal amplification by releasing reporter molecules only after a specific recognition of the analyte has taken place in an independent, separate step at the pore openings. On the other hand, the employment of tailored capture materials for the selective interaction with the released reporter molecules allows concentrating, i.e. focusing the latter for more efficient detection and to create selective multi-spot detection zones. That renders the simultaneous detection of several reporter molecules at the same time in multiplexed detection of various analytes possible. Simultaneous multiplexing, although theoretically possible, has not yet practically been realized because of the difficulty of separating different analytes and/or indicator molecules on a test strip or in a lateral flow device. According to typical embodiments the reporter comprises a dye, a fluorescent substance, a fluorescent ion, an ion of a rare earth element, or any combination thereof, to name a few. The reporter is selected to be optically detectable, directly or indirectly, at least after being trapped by the capture material.

According to an embodiment a test strip is suggested, wherein the pore-closing material is non-covalently bound to the sensing material, and detaches from the sensing material if bound by the analyte.

Advantageously, a non-covalent bond of the pore closing material to the mesoporous inorganic material facilitates unhindered diffusion of the reporter from inside of the pores into the solvent stream. On the other hand, the pore closing material, i.e. the "gate", itself can easily diffuse without any steric hindrance and the specific binding of the analyte is facilitated. In comparison to a covalently linked gate, the process of analyte-binding is faster and its specificity is preserved.

According to an embodiment a test strip is suggested, wherein the optical reporter comprises a fluorescent dye, a colored dye or a luminescent inorganic fluorescent ion of a rare earth element, e.g. an europium ion, typically in the form of a complex with organic sensitizer ligands.

Advantageously, fluorescent dyes allow exquisite sensitive and selective optical detection. If used in the form of complexes with organic ligands, ions of rare earth elements, e.g. europium, terbium, ytterbium, yttrium, or gadolinium, to name a few, show characteristic and narrow emission lines of atomic emission and then are detectable as well quite selectively and with high sensitivity.

According to an embodiment a test strip is suggested, wherein the reporter comprises a rhodamine, fluorescein, styryl, cyanine and polymethine, pyridinium, pyrylium, thiopyrylium, ruthenium, osmium or iridium complexes, luminescent complexes of rare earth elements (such as europium or terbium) and squarylium derivative. Additionally, all neutral, cationic and anionic derivatives of coumarin, dipyrromethene or BODIPY, pyrromethene, benzofuran, pyridine, naphthalimide, benzoxazole, benzoxadiazole, benzindole, DAPI, stilbene, oxazine, perylene, azulene, styryl base, phycoerythrin, squaraine, porphyrine, and phthalocyanine dyes.

Advantageously, most of these fluorescent and luminescent materials and compounds are commercially available and, therefore, appropriate optical and spectrophotometric equipment for their detection is also available.

According to an embodiment a test strip is suggested, wherein the capture material is selected from a molecular imprinted polymer, a polyionic liquid, a polyelectrolyte or a chemically functionalized mesoporous material comprises a functional group selected from a thiol, an isocyanate, an amino-group, a hydroxyl-group, an epoxy-group or a carboxylic acid group at the surface.

Advantageously, the capture material is adapted to specifically bind the reporter. The affinity of the capture material for the reporter may be due, e.g., to electrostatic interaction, selective affinity binding, hydrophobic interaction, nonspecific physicochemical adsorption or a mixed-mode mechanism. Functional groups for modifying a mesoporous material can be selected from, e.g., hydroxyl-, carboxyl-, epoxy-, amino-, sulfhydryl-groups or charged functional groups such as quarternary ammonium group.

According to an embodiment a test strip is suggested, wherein the capture material is selected from a molecular imprinted polymer and the molecular imprinted polymer is generated by polymerization of one or more types of monomers selected from: acrylamide, vinyl pyridine, N-isopropylacrylamide, 2-hydroxyethyl methacrylate, methyl methacrylate, benzyl methacrylate, methacrylate, methacrylamide, N,N'-dimethyl methacrylamide, vinylalcohol, vinylimidazole; by crosslinking with a crosslinking agent, the crosslinking agent selected from: ethylene dimethacrylate, ethylene glycol dimethacrylate, poly(acrylic acid), a bis($\beta$-hydroxyethyl) sulfone, trimethylolpropane trimethacrylate or, e.g., pentaerythritol triacrylate.

Advantageously, these polymers can be imprinted, e.g. with dyes, such as rhodamine or fluorescein, and bind such reporters quite strongly without causing any significant background signal. Positively charged dyes can be used as well for imprinting.

According to an embodiment a test strip is suggested, wherein the capture material is selected from a polyionic liquid (PIL) or polyelectrolyte, wherein the polyelectrolyte typically comprises polycations or polyanions such as for instance poly(diallyldimethylammonium chloride), poly(allylamine) hydrochloride, polyacrylic acid, poly(vinylpyrrolidone) (PVP), poly(sodium styrene sulfonate) (PSS), cyclodextran or polydextran.

Advantageously, these polyelectrolytes ensure a strong binding of the reporter even in buffered solutions (using high concentrations of the polyelectrolyte). Polycationic or polyanionic macromolecules can easily be applied to the matrix for fabricating the detection zone. Another advantage is that polyelectrolytes can interact selectively with anionic or cationic dyes.

According to an embodiment a test strip is suggested, wherein the test strip further comprises an absorption zone, the absorption zone being arranged downstream of the detection zone and adapted to absorb the solvent.

Advantageously, a steady stream of flowing solvent can be obtained. Reporters which have been released at the reporter release zone can reach the detection zone or, alternatively, each of the detection zones.

According to an embodiment a test strip is suggested, wherein an area of the test strip comprising at least one or more detection zones is surrounded by a barrier. The barrier either locally closes the pores of the porous matrix and/or locally modifies a wettability of the porous matrix for the solvent. The barrier thus forms a channel in the porous matrix. According to a modification of this embodiment, the fabricated channel may connect the sample application zone, the reporter release zone, and the detection zone. The sample application zone, the reporter release zone and the detection zone(s) may be arranged behind each other in the flow direction of the solvent.

Advantageously, a channel formed within the porous matrix facilitates a directed stream of the liquid phase or solvent. A standardized shape of such channels allows standardized streaming conditions for the solvent used as the mobile phase and allows comparing different lateral flow strips and hence, standardized assays.

According to an embodiment a test strip is suggested, wherein the barrier comprises a wax. Alternatively, a functional group, provided e.g. by a silane which is bound to the porous matrix, may alter or limit the wettability of the matrix and thus shape a channel-like structure or pattern within the porous matrix.

Advantageously, the mentioned materials can be used to effectively fabricate channels on/in cellulose and glass fibre paper, as well as in other porous matrix materials.

According to an embodiment a test strip is suggested, wherein the sensing material comprises a mesoporous inorganic material.

Advantageously, a plethora of mesoporous inorganic materials are accessible and even commercially available. Said mesoporous materials can easily be filled with a reporter substance, e.g. a fluorescent dye or ion.

According to an embodiment a test strip is suggested, wherein the mesoporous inorganic material comprises silica, alumina, $TiO_2$, carbon, carbonitride, silicon carbide, silicon oxycarbide, silicon carbonitride, silicon nitride, silicon oxynitride, silicon aluminum nitride, or silicoboron carbonitride.

Advantageously, these materials are chemically inert, can easily be loaded with reporter molecules, e.g. dyes, and can be easily modified with appropriate capping materials to generate analyte-adapted sensing materials.

According to an embodiment a test strip is suggested, wherein the porous matrix is selected from a paper, a felt, a nonwoven, a fibre, a pressed or sintered powder, a cloth, or a tissue, wherein the paper, the felt, the nonwoven, the fibre, the pressed or sintered powder, the cloth, and the tissue comprise at least one of a polymer, e.g. a cotton or a cellulose, a glass, a ceramic, a carbon, a graphene, a mineral, or a metal.

Advantageously, an appropriate material may be selected to be wettable by the actual solvent or liquid phase of the sample to be analyzed.

According to an embodiment a test strip is suggested, wherein the test strip comprises one reporter release zone and between 2 and 7 detection zones. Such multiple detection zones herein can also be described as a structured detection zone.

Advantageously, several detection zones allow applying principles of pattern recognition and thus automated sample analysis and multiplexing. A multiplex assay is a type of assay used in analytical chemistry, clinical chemistry, and biochemistry to simultaneously measure multiple analytes in a single run/cycle of the assay. It is distinguished from procedures that measure one analyte at a time. The advantage of using several detection zones is that a multiplexing assay is possible to perform in a single channel. In absence of these detection zones, different channels are necessary to produce a multiplexing.

According to an embodiment a test strip is suggested, wherein the test strip at least at the reporter release zone and/or at the detection zone comprises at least two matrix layers.

Advantageously, test strips can be prepared easily, e.g. by sandwiching matrix layers which comprise the specified zones (e.g. a detection zone) between two unmodified matrix layers which cover and enclose the specified zones. Strips can also be prepared through lamination, using capillary forces to allow the flow and the diffusion of reporter through different zones.

According to an embodiment a shape of the test strip deviates from a non-square rectangle and comprises a square rectangle or any other shape. For instance, the test strip may comprise at least a section of a circle or of a triangle.

Although an oblong shape of the test strip may be preferred as the most common format in lateral flow assays, other shapes of the porous substrate can be used to generate a directed current of the streaming liquid phase which carries the used reporter(s) to the detection zone(s). A combination of several patterns can be used to generate a proper flow of solvent in the strip.

According to an embodiment the sample application zone is arranged on top of the reporter release zone. It may be arranged directly on top of the reporter release zone or form a stack together with an intermediate matrix layer.

Advantageously, different porous matrix materials can be selected for the different zones. According to this modification, the indicated zones, i.e. the sample application zone, the reporter release zone and the at least one detection zone are arranged along a current of the solvent, the solvent carrying the reporter(s) to the detection zone(s).

According to an embodiment a method for detecting an analyte is proposed, the method comprising:
  providing a test strip according to any of the embodiments described above;
  applying a sample to the sample application zone of the test strip;
  detecting a presence and/or a quantity and/or a concentration of the optical reporter in the at least one detection zone;
  determining a presence and/or a concentration of the analyte in the sample.

Advantageously, the method is suitable for multiplex assay formats.

According to an embodiment, the proposed method further comprises providing a liquid for generating a continuous or discontinuous fluid stream from the sample application zone to the reporter release zone and from the reporter release zone to at least one detection zone. The liquid may be selected from a solvent for the analyte.

The liquid can be provided by the liquid phase of the sample, e.g. a solvent. Alternatively, the liquid, e.g. a solvent for the analyte, can be added in a separate step, after the sample has been applied. Typically, the liquid generates a current (liquid stream) carrying the analyte from the sample application zone at least to the reporter release zone. Further, a current (liquid stream) is generated which is directed from the reporter release zone to the detection zone. Depending on the amount of liquid, there can be a continuous liquid stream from the sample application zone through the reporter release zone to the detection zone. However, it is also possible to have a first stream which is directed from the sample application zone to the reporter release zone, and which may be driven by gravitational forces and/or by capillary forces, and a second stream. The second stream is typically driven by capillary forces and directed from the reporter release zone toward the detection zone and may even reach an absorbing pad downstream thereof. Advantageously, the combination of different solvents may enable the detection of analyte suspensions.

According to an embodiment a method for detecting an analyte is proposed, wherein the optical reporter is a fluorescent dye and the detecting is accomplished by a fluorescence measurement with a hand held device, i.e. portable device.

Advantageously, said detection method may be applied in the field, on the spot, without sophisticated equipment even in settings with no or minimal infrastructure.

According to further embodiments, a portable device such as a smartphone, tablet, or mobile communication and computing device may be used to collect an optical signal, e.g. a photoluminescence and determine whether the photoluminescence in a selected detection zone is indicative of the presence of a certain analyte.

Some smartphone models can be equipped with means to allow users and/or programmers to access or control the exposure and shutter speed of the camera. It can be advantageous to obtain suitable raw images from camera acquisition, e.g. images that do not suffer from auto-exposure compensation algorithms. Such algorithms, which may be integrated into a smartphone hardware or software, can be convenient for an end user as a hobby photographer, but may pose problems when using the smartphone for chemical analysis and chemometric techniques. For example, the lux amount received by the camera's detector such as CMOS or CCD can possibly be automatically tuned to match certain predefined lux criteria. Using such values instead of properly calibrated and corrected ones can lead to misleading and false results.

Therefore, according to a further embodiment, the proposed method can include comparing the photoluminescence in a detection zone to a calibration value; such as comparing a signal, such as the luminescence, to a reference. The reference may be stored data or a reference spot on test strip, for example.

Furthermore, a ratio of the signal intensity generated at a detection zone to the signal intensity generated at the reporter release zone can be used for semi-quantitative detection of an analyte. In particular, the quotient of fluorescence intensity at detection zone divided by the sum of fluorescence intensity at detection zone plus fluorescence intensity at reporter release zone, i.e. the equivalent to the ratio of released reporter divided by the total amount of reporter can be used for semi-quantitative detection of an analyte. Also a ratio of fluorescence values obtained at different excitation or emission wavelengths may be used. According to typical embodiments, digital images of the strips or at least of the detection zone can be obtained with a digital camera. The digital images or sections thereof can be processed using the open source image processing program ImageJ (https://imagej.net/). Such processing can be used both for internal referencing and for semi-quantitative detection.

Each embodiment described above may be combined with any other embodiment or embodiments unless clearly indicated to the contrary.

The proposed embodiments comprise the design of a test strip or a dip stick which is adapted for a lateral flow assay (see FIG. 1) and comprises: first, a section for sample introduction (i.e. the sample application zone); second, a section or segment containing a mesoporous hybrid sensing material able to specifically interact with the analyte (i.e. the reporter release zone); and third, a section or segment containing a capture material able to specifically interact with the optical reporter molecule released from the sensing material (i.e. the detection zone). This section can contain more than one capture material with the aim to retain different reporters (e.g. dyes, fluorescent substances, fluorescent ions, ions of a rare earth element, or their combination, to name a few) as reporter molecules when a mixture of sensing materials is used.

Once the flow is initiated for a lateral flow or dip-stick assay format, the solvent can transport the analytes from zone 1 to zone 2, in which the sensing material is deposited and in which release of the reporter molecule from the sensing material will happen only in presence of the corresponding analyte. The reporter will then migrate from zone 2 toward the respective detection zone 3. There the reporter(s) will be retained depending on its(their) specific chemical nature, using various macromolecules or capture materials chosen to be complementary to the reporter. Due to the interaction of the reporter with the capture material the reporter will typically be immobilized in that detection zone.

The technical objective of the embodiments is to use several capture materials immobilized in the detection zone of test strips with the aim to provide a label-free, potentially multiplexed detection on lateral flow devices. These immobilized macromolecules or capture materials will be able to selectively interact with the optical reporter. The optical reporter is already selectively released from the sensing material by the analyte which moves from the sample injection zone (i.e. sample application zone) toward the detection zone(s). The advantage of this method is that the reporter released from the pores of the gated material in the course of a successful detection event is dedicatedly captured only at a well-defined location on the strip, i.e. in the detection zone or in one of various detection zones. That improves not only the selectivity but also the sensitivity due to the focusing of the reporter in a well-defined and confined area.

The porous matrix materials can comprise:
a) Cellulose, cotton, cloth, graphene, carbon nanotubes (CNT); glass fibre paper, glass or polymers modified with certain organic groups able to interact specifically with the optical reporter.
b) Certain molecularly imprinted polymers (MIPs) or imprinted gels for the specific detection of the optical reporter, cationic or anionic polyelectrolytes, silica or alumina mesoporous materials (e.g., $SiO_2$-type MCM-41, HMS, MSU-n, MSU-V, FSM-16, KSW-2, SBA-n (n=1, 2, 3, 8, 11-16), FDU-n (12, 14, 15, 16), UVM-7, UVM-8, M-UVM-7 or M-UVM-8, $Al_2O_3$-type MCM-41) modified with certain organic groups using several organosilanes (e.g., amino groups using 3-aminopropyltriethoxysilane (APTES) or carboxylic acid groups by a ring opening linker elongation reaction of the amino groups with succinic anhydride).

The described embodiments have versatile application areas for the detection of small molecules in the medical, environmental, safety and food diagnostic industries. With the aim to demonstrate the feasibility of suggested embodiments, some examples describing used laboratory methods and materials are given below.

EXAMPLES

The synthesis of MCM-41 and SBA-15 type mesoporous materials was performed following previously reported procedures. For the MCM-41, n-cetyltrimethylammonium bromide (CTAB, 1.00 g, 2.74 mmol) was first dissolved in 480 mL of milliQ water. Then, 3.5 mL of NaOH (2.00 M in milliQ water) was added to the CTAB solution, followed by adjusting the solution temperature to 80° C. TEOS (5.00 mL, $2.57 \cdot 10^{-2}$ mol) was then added dropwise to the surfactant solution. The mixture was stirred for 2 h to give a white precipitate. Finally, the solid product was centrifuged, washed with milliQ water and ethanol, and dried at 60° C. With the aim to remove the surfactant, the sample was calcinated 8 h at 560° C.

SBA-15 was synthesized with triblock poly(ethylene oxide)-poly(propylene oxide)-poly(ethylene oxide) (EO 20-PO 70-EO 20, P123) copolymer as a structure directing agent and tetraethylorthosilicate (TEOS) as a silica source. In a typical synthesis, 4.0 g (0.69 mmol) of P123 was dissolved in 120 mL of water and 19.41 mL of HCl and then stirred at 35° C. for one hour in order to dissolve the polymer. Then, 9.15 mL of TEOS (41 mmol) was added dropwise into the homogeneous solution with stirring at 35° C. for 24 h. The obtained gel was aged at 100° C. in a Teflon flask without stirring for another 24 h. The white solid obtained was filtered, washed with distilled water and air-dried at 70° C. in a vacuum for 12 h. Finally, the template was removed by calcination during 8h at 560° C.

In the following, materials for the detection of dyes (reporters), especially the synthesis of APTES-MCM and APTES-SBA materials is described. Materials were modified according to reported procedures. A suspension of 100 mg of MCM-41 or SBA-15 in 2.5 mL of acetonitrile (MeCN) and an excess of 3-aminopropyltriethoxysilane (APTES; 186.3 µL, 8 mmol $g^{-1}SiO_2$) was stirred at room temperature during 5.5 h in an argon atmosphere. Then, the material was centrifuged for 5 min at ca. 10,000 rpm and washed two times with 1.5 mL of MeCN. Finally, the material was dried in a vacuum at 40° C. for 2 h, yielding the resulting materials APTES-MCM and APTES-SBA.

In the following, the synthesis of COOH-MCM is described. For the modification of MCM-41 with carboxylic acid groups, 50 mg APTES-MCM materials were suspended in 1.5 mL of EtOH, following reported procedures. 250 µL of a solution of succinic anhydride (100 mg $mL^{-1}$) were added to each of the suspensions prepared, and suspensions were left to stir overnight at 40° C. Then, the material was centrifuged for 5 min at ca. 10,000 rpm and washed two times with 1.5 mL of EtOH. Finally, the material was dried in a vacuum at 40° C. for 2 h, yielding the resulting material COOH-MCM.

In the following, the synthesis of PA-COOH-MCM and PVP-APTES-MCM is described. Poly(vinylpyrrolidone) 40 (PVP-40) and poly(diallyldimethylammonium chloride) (PDDAC) were chemically adsorbed to the surfaces of APTES-MCM and COOH-MCM, respectively. For the synthesis of PVP-APTES-MCM, 20 mg of APTES-MCM were suspended for 2 h in a solution of 25 mg $mL^{-1}$ of PVP-40 in $H_2O$ (1 mL). PA-COOH-MCM was prepared suspending 20 mg of COOH-MCM for 2 h in 1 mL of $H_2O$ containing 50 µL of a solution of 35% PDDAC in water. After 2 h, both suspensions were centrifuged for 5 min at ca. 10,000 rpm and washed two times with 1.5 mL of $H_2O$. Finally, the material was dried in a vacuum at 40° C. for 2 h, yielding the resulting materials PVP-APTES-MCM and PA-COOH-MCM.

In the following, the synthesis of APTES-cellulose paper (APTES-C) and APTES-glass fibre paper (APTES-GF) is described. Cellulose paper and glass fibre paper were modified with amino groups using 3-aminopropyltriethoxysilane (APTES). For that purpose, 20 pieces of the corresponding paper (2×0.5 cm) were suspended in 7 mL of toluene and 100 µL of APTES. Samples were stirred during 16 h at 80° C. The resulting amino-modified papers were collected and then washed 2 times with toluene and one time with EtOH, and were dried under vacuum for 3 h, obtaining the corresponding APTES-C and APTES-GF papers.

In the following, the synthesis of COOH-cellulose paper (COOH-C) and COOH-glass fibre paper (COOH-GF) is described. For the modification of APTES-C and APTES-GF paper with carboxylic acid groups, 5 pieces of each paper were mixed with 1.5 mL of EtOH, following reported procedures. 250 µL of a solution of succinic anhydride (100 mg $mL^{-1}$) were added to each of the mixtures prepared, and were left to stir overnight at 40° C. Then, the papers were removed and washed two times with 1.5 mL of EtOH. Finally, the papers were dried in a vacuum at 40° C. for 2 h, yielding the resulting papers COOH-MCM and COOH-SBA.

In the following, the synthesis of methacrylate-glass fibre paper (M-GF) is described. Glass fibre paper was modified with methacrylate groups following the same procedure described for APTES-GF but using 3-(trimethoxysilyl)propyl methacrylate instead of APTES, obtaining the papers M-GF.

In the following, the synthesis of selective polymer gels and polymer gels on paper for the detection of dyes is described. Particularly, the synthesis of FLU-M-GF, SURB-M-GF, SURG-M-GF, R6G-M-GF and RuBipy-M-GF is described. The imprinted paper gels on paper were prepared using the aqueous precipitation polymerization method following literature procedures. Typically, 10 pieces of M-GF (2×0.5 cm) were mixed with 6 mL of a PBS solution (20 mM; pH 7.2) containing acrylamide (AAm; 29.1 mg, 0.41 mmol) and N-isopropylacrylamide (NIPAAm; 46.4 mg, 0.41 mmol). 150 µL of a solution of 5 mM of the corresponding template molecule 2,7-dichlorofluorescein (FLU), sulforhodamine B (SURB), sulforhodamine G (SURG), rhodamine 6G (R6G) or ruthenium bipyridine (RuBipy) was added to the solution, and the mixture was incubated for 30 min with slow stirring at 25° C. to form complexes. After that, the cross-linker N,N'-ethylene bis(acrylamide) (EBAAm; 25.2 mg; 0.15 mmol) was added. After purging the mixture with $N_2$ for 1 h, polymerization was initiated by adding ammonium persulfate (APS; 6 mg) and N,N,N',N'-tetramethylethylenediamine (TEMED; 3 µL). The reaction was continued for 1 h at 25° C. under a $N_2$ atmosphere, observing the formation of the gel after 10 min. After 1 h of reaction, the resultant imprinted paper gels were collected by removing them from the gel, followed by extensive washing with NaCl solution (1 M) until complete removal of the unreacted monomers and templates. Finally, the corresponding papers were dried for 2 h in a vacuum, yielding the corresponding FLU-M-GF, SURB-M-GF, SURG-M-GF, R6G-M-GF and RuBipy-M-GF paper gels. In parallel, the gels FLU-MIG, SURB-MIG, SURG-MIG, R6G-MIG and RuBipy-MIG were dried overnight in a vacuum. The non-imprinted gels and paper gels (NIG and NIG-M-GF) were prepared in the same way except that no template was added during polymerization.

Further below, results of studies employing only the deposition of dyes on the interaction zone will be described.

In a first attempt, to initially check the efficiency of the materials prepared as detection zone(s) 3, merely various dye solutions were spotted onto the interaction zone 2 of the strips, not involving the more complex mesoporous hybrid sensing materials. Here, exemplary studies were performed with selected polyelectrolytes and mesoporous capture materials prepared on zone 3, employing both glass fibre and nitrocellulose membranes.

Figure 2:
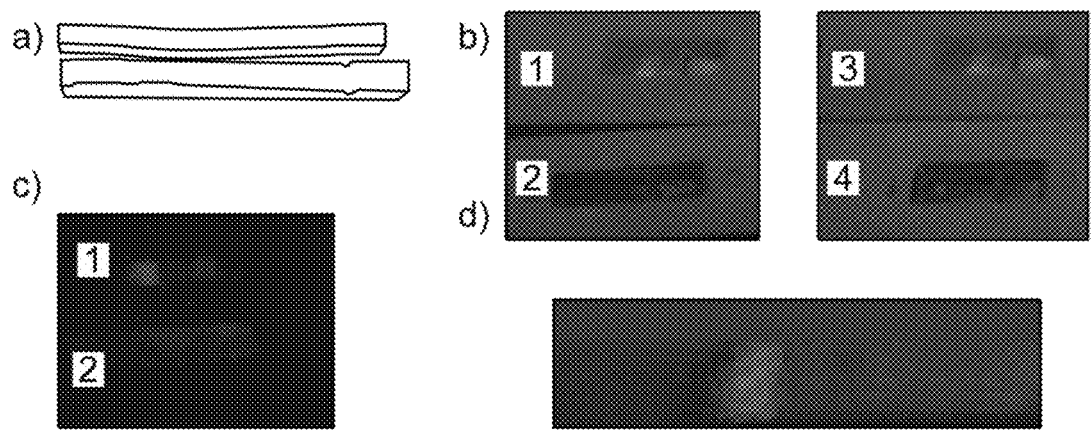
FIG. 2a shows a test strip or dip stick adapted for a lateral flow assay comprising a line of poly(diallyldimethylammonium chloride)=PDDAC which had been applied as a 17% solution over a width of 6 mm on the porous matrix to form a capture zone and containing 1 µL of a sulforhodamine B solution (SURB; 10 mg mL$^{-1}$ in $H_2O$) to simulate a reporter release zone at 2 cm from the bottom.
FIG. 2b shows a corresponding test strip after flow using $H_2O$ as solvent (1 and 2) and phosphate buffered saline=PBS (0.8 mM; 3 and 4) as solvent after 5 min (1 and 2) and 1 h (3 and 4) of flow.
FIG. 2c shows a test strip containing a PDDAC line (35% 3 mm) as capture zone after 3 min (1) and 10 min (2) of flow using PBS as solvent (0.8 mM, pH 7.5).
FIG. 2d shows a test strip containing a PDDAC line (35%, 6 mm) as capture zone after 20 min of flow with PBS buffer.

In the following, studies with polyelectrolytes applied as capture materials, i.e. for the formation of a detection zone will be described. A PDDAC solution (17%) was employed to create a line with a thickness of 0.5 cm (3 spots of 1 µL) on a glass fibre membrane, 4 cm from the bottom of the membrane, resembling the first detection zone (FIG. 2a). 1 µL of a sulforhodamine B solution (SURB; 10 mg mL$^{-1}$ in H$_2$O) was spotted on the interaction zone at 2 cm from the bottom, and the strip was put into a LF cassette (lateral flow casette), using a cotton paper as sample and adsorbent pads. The flow was produced by pipetting of 100 µL of H$_2$O (FIG. 2b) and PBS buffer (FIG. 1c; 0.8 mM, pH 7.5). The flow was monitored by taking photographs under UV light ($\lambda_{ex}$ 254 nm). Only in case of H$_2$O, the detection zone was able to efficiently retain the dye in the zone even after 1 h (FIGS. 2b/1 and 3). However, when buffer was used we observed that the retention of the dye was only efficient during the first 5 min (FIG. 2b/2); afterwards the polyelectrolyte line containing the dye was also starting to move with the flow to the end of the strip, smearing the dye (FIG. 2b/4).

In a further experiment, a more concentrated solution of PDDAC (35%) was used to try to improve the "immunity" against PBS (0.8 mM, pH 7.5); PBS buffer is a very frequent solvent and often necessary for successful performance of biomacromolecules in assays. For that purpose, a thinner line of 3 mm of polymer was spotted onto the paper and 1 µL of SURB (10 mg mL$^{-1}$ in H$_2$O) was used. In that case, we observed that the dye was flowing and retained in a small area. However, again, the retention was only effective for 3 min (FIG. 2c/1). Afterwards, the dye continued to migrate with the flow (FIG. 2c/2).

In a further experiment, we prepared a thicker line (ca. 6 mm) of a solution of 35% of PDDAC (35%). Here, we observed that the flow stopped once it reached the region of the polymer line, pre-concentrating SURB at the beginning of the line (FIG. 2d). With the experiments performed we can conclude that the employment of polyelectrolytes as capture material is efficient for non-buffered solvents or using buffers in an assay performing the assay in less than 5 min. That means that with buffer the retention is only effective during the first minutes, afterwards retention is not effective anymore. In all the cases flow is really fast, within ca. 1 minute the strip is completely wet and dye starts to accumulate on polymer line.

In the following, studies with mesoporous materials as capture material will be described. In a first experiment, the effect of the mesoporous scaffold employed for the preparation of the capture materials was tested. For this attempt, 2,7-dichlorofluorescein was employed as reporter dye. Several nitrocellulose strips containing hydrophobic wax patterns were prepared, defining several zones on the strip. Nitrocellulose strips of 4.5×0.5 cm were printed and were heated 1 min at 105° C. in an oven to guarantee penetration of the wax into the paper, resulting in paper-thick barriers in the membrane (FIG. 3a). 1 µL of a solution of 2,7-dichlorofluorescein (FLU; 10 mg mL$^{-1}$) was deposited on the reporter release zone 2), whereas 2.5 µL of an aqueous suspension of 10 mg mL$^{-1}$ of the corresponding APTES-MCM and APTES-SBA materials were suspended on the detection zone 3). The efficiency of the capture materials deposited in zone 3) was tested adding on sample application zone 1) 15 µL of PBS solution (80 mM; pH 7.5).

Figure 3:
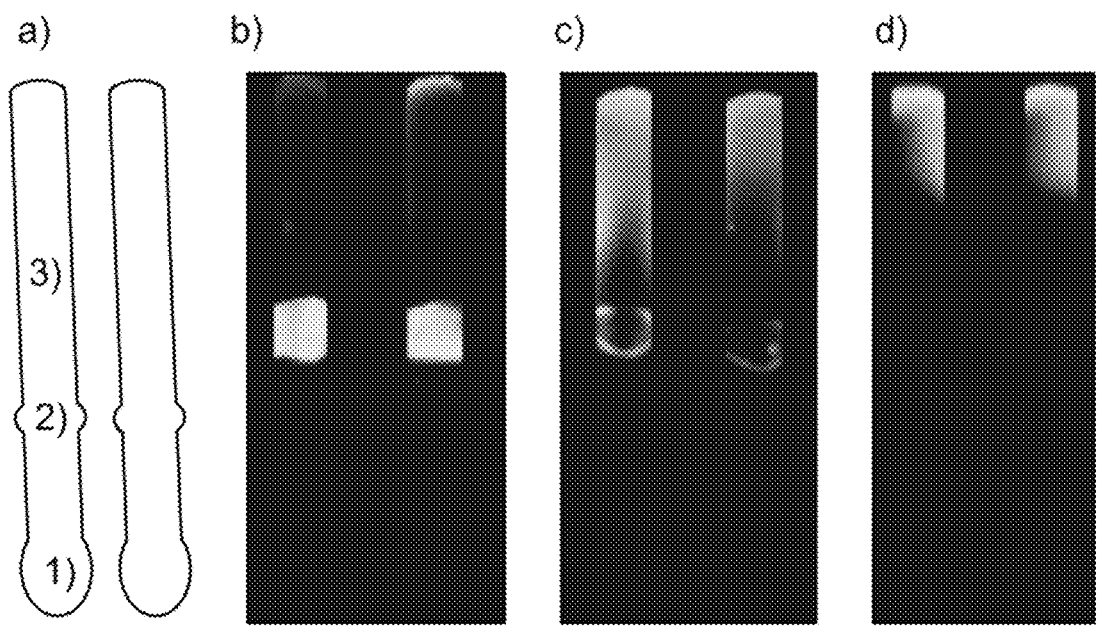
FIG. 3a shows a photograph of nitrocellulose strips modified with hydrophobic wax barriers containing the sample application zone 1), the reporter release zone 2), containing here the dye 2,7-dichlorofluorescein, and the detection zone 3), containing APTES-modified mesoporous materials. Therein APTES stands for (3-aminopropyl)triethoxysilane.
FIG. 3b shows photographs under home-made UV lamp after the flow of 2,7-dichlorfluorescein (FLU) on strips containing APTES-MCM in the detection zone 3). MCM stands for mesoporous silica material MCM-41. Corresponding strips with APTES-SBA in detection zone 3) are shown in FIG. 3c and with COOH-MCM in detection zone 3) in FIG. 3d after flow. Therein SBA stands for mesoporous silica material SBA-15. COOH-MCM stands for COOH-functionalized MCM. Used abbreviations will be explained further below.

During flow of the dye solution along the strip, capture of FLU, a negatively charged dye, was expected to happen in the amino-modified materials in detection zone 3), because these group are largely protonated at neutral pH and shall be able to capture negative species because of electrostatic forces. After 2 min, the strips were placed under a homemade 3D-printed lamp equipped with two LEDs ($\lambda_{exc}$ 470 nm and 505 nm) as excitation source and filters (532 nm cut-off and 550 nm long-pass), and some photographs were taken to observe the capture efficiency of materials in detection zone 3). FIG. 3b shows strips containing APTES-MCM in zone 3 whereas FIG. 3c shows strips containing APTES-SBA. As can be seen, the MCM-41 scaffold is able to retain much more dye in comparison with SBA-15.

Considering that MCM-41 was much more efficient, a similar experiment was conducted with COOH-MCM instead of APTES-MCM in detection zone 3). After the corresponding flow, no FLU was retained in detection zone 3, most likely because of electrostatic repulsion between the negatively charged material and the anionic dye employed (FIG. 3d).

Figure 4:
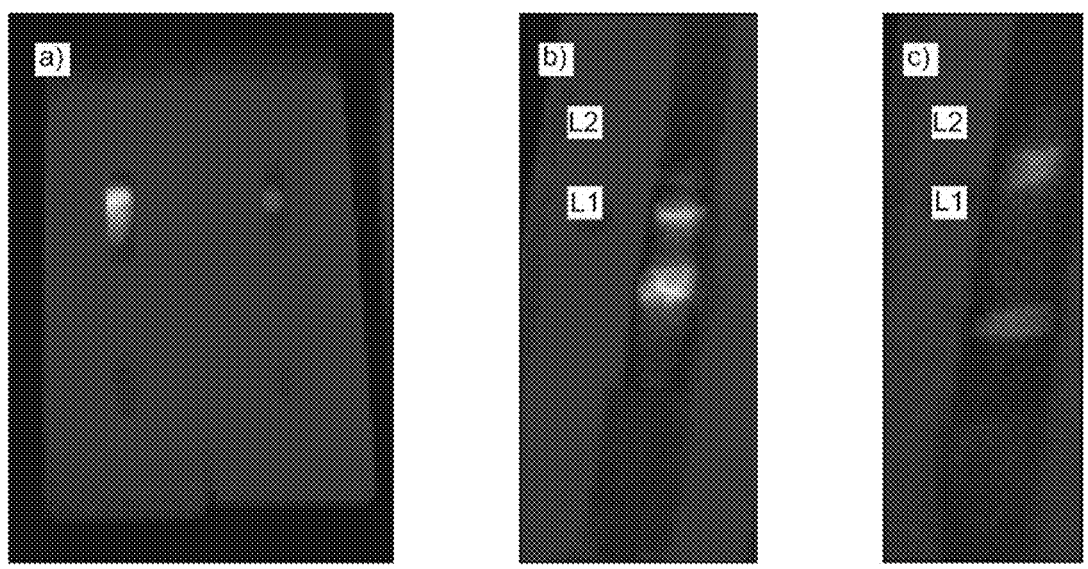
FIG. 4a shows a photograph of strips under UV light comprising a line of APTES-MCM as the capture zone and the dyes SURB (left) and FLU (right) in a concentration of 1 mg mL$^{-1}$ as applied in the reporter release zone 2 after flowing with PBS (80 mM) as solvent.
FIG. 4b shows a photograph of the strip under UV light containing a line of COOH-MCM (L1) and APTES-MCM (L2) as detection zones and a mixture of dyes rhodamine 6G (R6G) and FLU (1 mg mL$^{-1}$) in reporter release zone 2 after flowing with 80 mM PBS as solvent.
FIG. 4c shows corresponding photographs of the strip under UV light containing a line of PVP-APTES-MCM at L1 and PA-COOH-MCM at L2 as detection zones and a mixture of dyes R6G and FLU (1 mg mL$^{-1}$) in reporter release zone 2 after flowing with 80 mM PBS as solvent. Therein PVP-APTES-MCM stands for poly(vinylpyrrolidone)-(PVP) modified APTES-MCM and PA-COOH-MCM stands for PDDAC-modified COOH-MCM. Note that R6G is more similar in colour and fluorescence to FLU than to SURB.

To avoid retention of the dye on nitrocellulose membranes when using cationic dyes, a glass fibre membrane was also tested. Due to the higher hydrophilicity of the paper, the spots of materials were more concentrated and it was necessary to spot 2 times 10 µL of a suspension of 10 mg mL$^{-1}$ of APTES-MCM to create a proper line. FIG. 4a shows the efficiency of the APTES-MCM line after the flow of the strips, containing 1 µL of SURB or FLU in reporter release zone 2. The retention of the dye was effective even after a couple of hours.

Considering the results found, in a second experiment we used COOH-MCM and APTES-MCM with the aim to create 2 lines on the detection zones, i.e. to fabricate two separate detection zones, and separate one anionic from a cationic dye. A mixture of two different dyes was spotted on the interaction zone, a negatively charged dye (FLU) and a positive charged dye (R6G; 1 µL 1 ppm). COOH-MCM was spotted on a line at a distance of ca. 3 cm from the bottom (L1) whereas APTES-MCM was spotted at 4 cm from the bottom (L2). After the flow, a selective fluorescence corresponding only to R6G in L1 and FLU in L2 was observed (FIG. 4b).

Finally, we tested the materials PVP-APTES-MCM and PA-COOH-MCM for the retention of the dyes Rhodamine 6G and 2,7-dichlorofluorescein in a similar way to the studies done with COOH-MCM and APTES-MCM. For that purpose, PVP-APTES-MCM was used to create the L1, whereas PA-COOH-MCM was used to create L2. As can be seen on FIG. 4c, similar results were found as the previous experiment.

In the following, studies with modified cellulose and glass fibre papers as porous matrix will be described. In a first experiment, the influence of the nature of the paper employed was tested. For these experiments, FLU was used as model dye. Thus, pieces of 0.5×0.5 cm of APTES-C and APTES-GF papers were fixed between two membranes of GF paper, representing detection zone 3, equalling a total strip length of 3.5 cm. 1 µL of a FLU solution (10 mg mL$^{-1}$) was spotted at ca. 1 cm from the bottom (FIG. 5a), simulating the reporter release zone 2. Strips were left in a LF cassette. After addition of 100 µL of PBS (80 mM, pH 7.5), the flow along the strip was monitored under UV light by a similar procedure as described before. In both cases, a retention of FLU with time was observed (FIGS. 5b and 5c/1 and 5c/2), being longer retained on APTES-C compared with APTES-GF. To study the selectivity of the papers, the same experiment was carried out with a piece of COOH-GF (FIGS. 5b and 5c/3), In that case, a fast flow of FLU along the membranes was observed; retention was absent.

Figure 5:
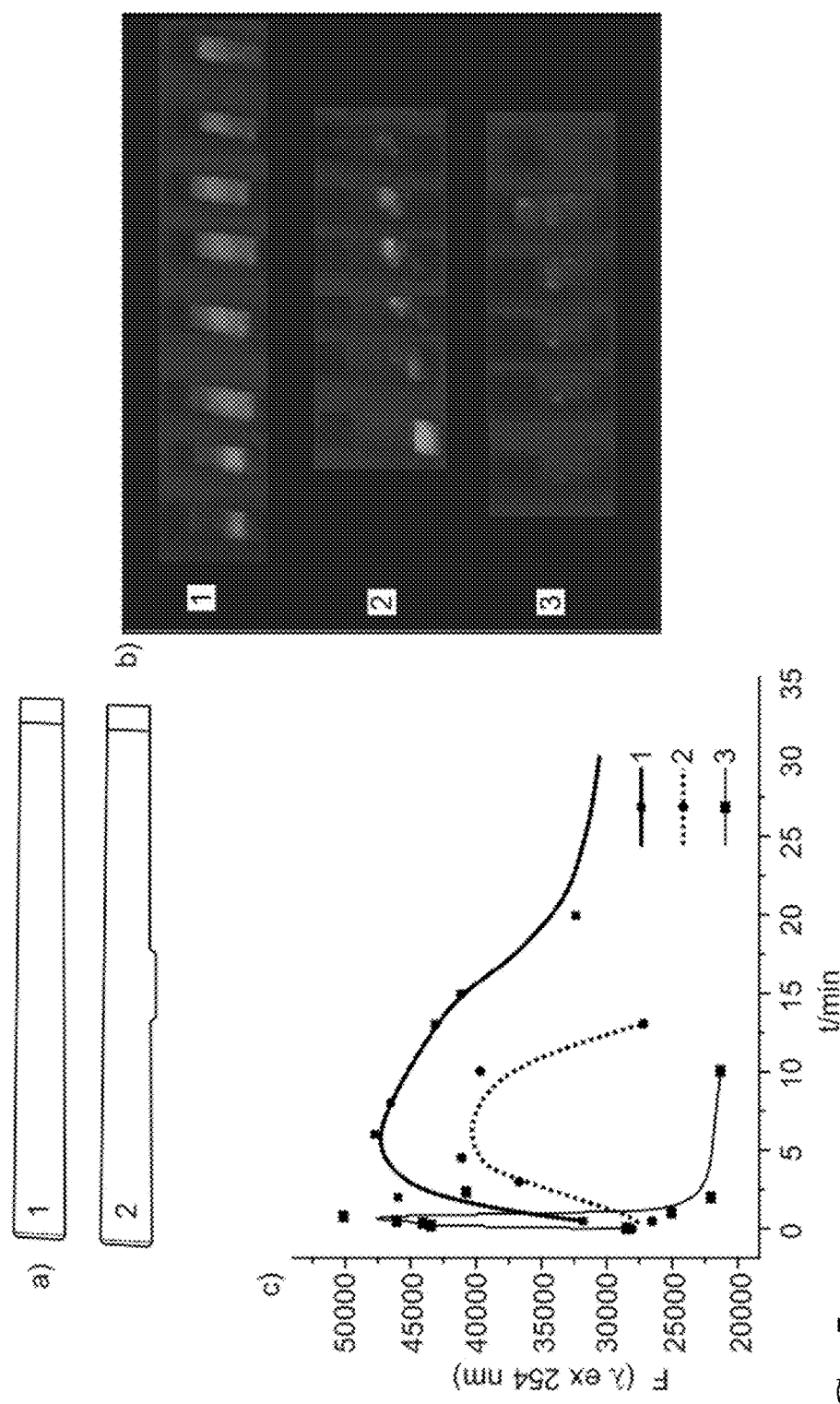
FIG. 5a shows a photograph of the strips containing a piece of APTES-C (1) and APTES-GF (2) paper at the capture material in the detection zone 3 and a spot of FLU dye (10 mg mL$^{-1}$) on the reporter release zone 2. Therein APTES-C stands for APTES-modified cellulose paper and APTES-GF stands for APTES-modified glass fibre paper.
FIG. 5b shows a photograph of the corresponding strips under UV light containing APTES-C (1), APTES-GF (2) and COOH-GF (3) at the detection zone 3 during the flow as a function of time.
FIG. 5c shows the integrated fluorescence of the area of the capture zones as a function of the time evaluated using ImageJ software for the capture materials APTES-C (1), APTES-GF (2) and COOH-GF (3). Abbreviations will be explained further below.

To quantify the amount of fluorescent dye retained, the integrated fluorescence of the area of the detection zones was evaluated as a function of time using the ImageJ software. The results are depicted in FIG. 5c.

Figure 6:
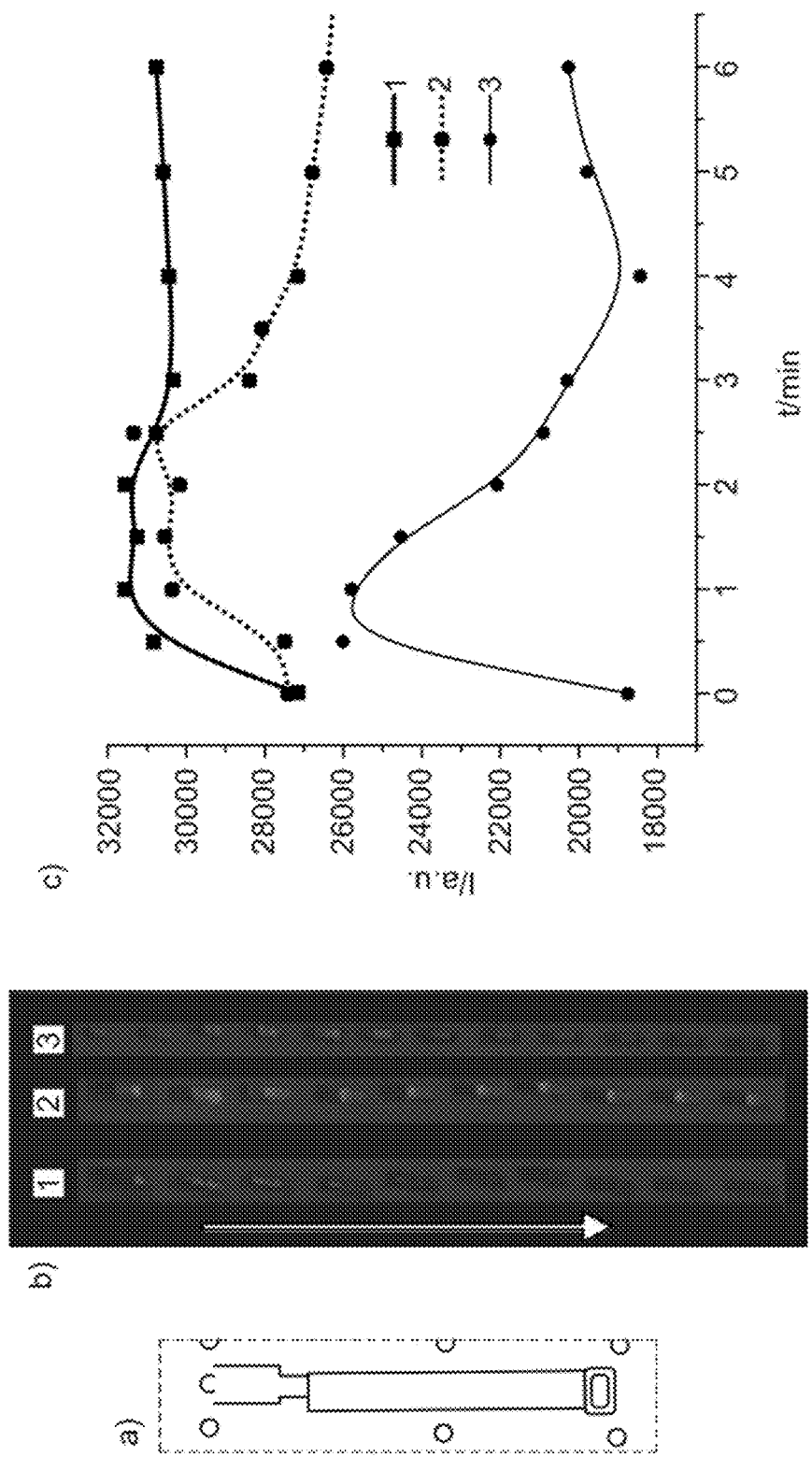
FIG. 6a shows a photograph of a strip containing a piece of FLU-M-GF paper at the capture zone and a spot of FLU dye on the reporter release zone (simulated interaction zone).
FIG. 6b shows a photograph of the corresponding strips under UV light after certain time intervals containing 1) NIG-M-GF and 2) FLU-M-GF using FLU as dye, and 3) FLU-M-GF using SURB as dye. Therein NIG-M-GF stands for non-imprinted gel-modified 3-(trimethoxysilyl)propyl methacrylate-modified glass fibre paper. FLU-M-GF stands for FLU-imprinted M-GF.
FIG. 6c shows a graph of corresponding integrated fluorescence intensities in arbitrary units of the area of the detection zones as a function of time evaluated using ImageJ software for the capture materials 1) NIG-M-GF and 2) FLU-M-GF using FLU as dye, and 3) FLU-M-GF using SURB as dye. These dyes were applied as aqueous solutions for simulating released reporter from the reporter release zone as will be explained further below.

In the following, studies with polymer gels on paper will be described. From the papers prepared with imprinted gels, we selected FLU-M-GF to perform the experiments, using also NIG-M-GF as a reference. A piece of 0.5×0.5 cm of NIG-M-GF or FLU-M-GF was fixed as capture zone between two membranes of GF paper, resulting in a strip of a total length of 3.5 cm. 1 µL of a FLU solution (10 mg mL$^{-1}$) was spotted at ca. 1 cm from the bottom (interaction zone; FIG. 6a). To check the selectivity of the FLU-M-GF against other dyes, another strip containing FLU-M-GF at the detection zone was prepared and 1 µL of a SURB solution (10 mg mL$^{-1}$) instead of FLU was spotted on the reporter release zone.

The strips were left in a LF cassette and after addition of 100 µL of PBS, the development of the flow along the strip was monitored under UV light, by a similar procedure as described before. FIG. 6b shows the corresponding flow of the three strips prepared as a function of time for 1) NIG-M-GF and 2) FLU-M-GF using FLU as dye, and 3) FLU-M-GF using SURB as dye. As can be seen, the retention of FLU was only effective using FLU-M-GF, whereas SURB was not retained by FLU-M-GF. The amount of fluorescence retained on NIG-M-GF and FLU-M-GF as a function of time was also quantified using the ImageJ software. The results agree with the fluorescence observed under the UV-lamp (FIG. 6c).

Figure 7:
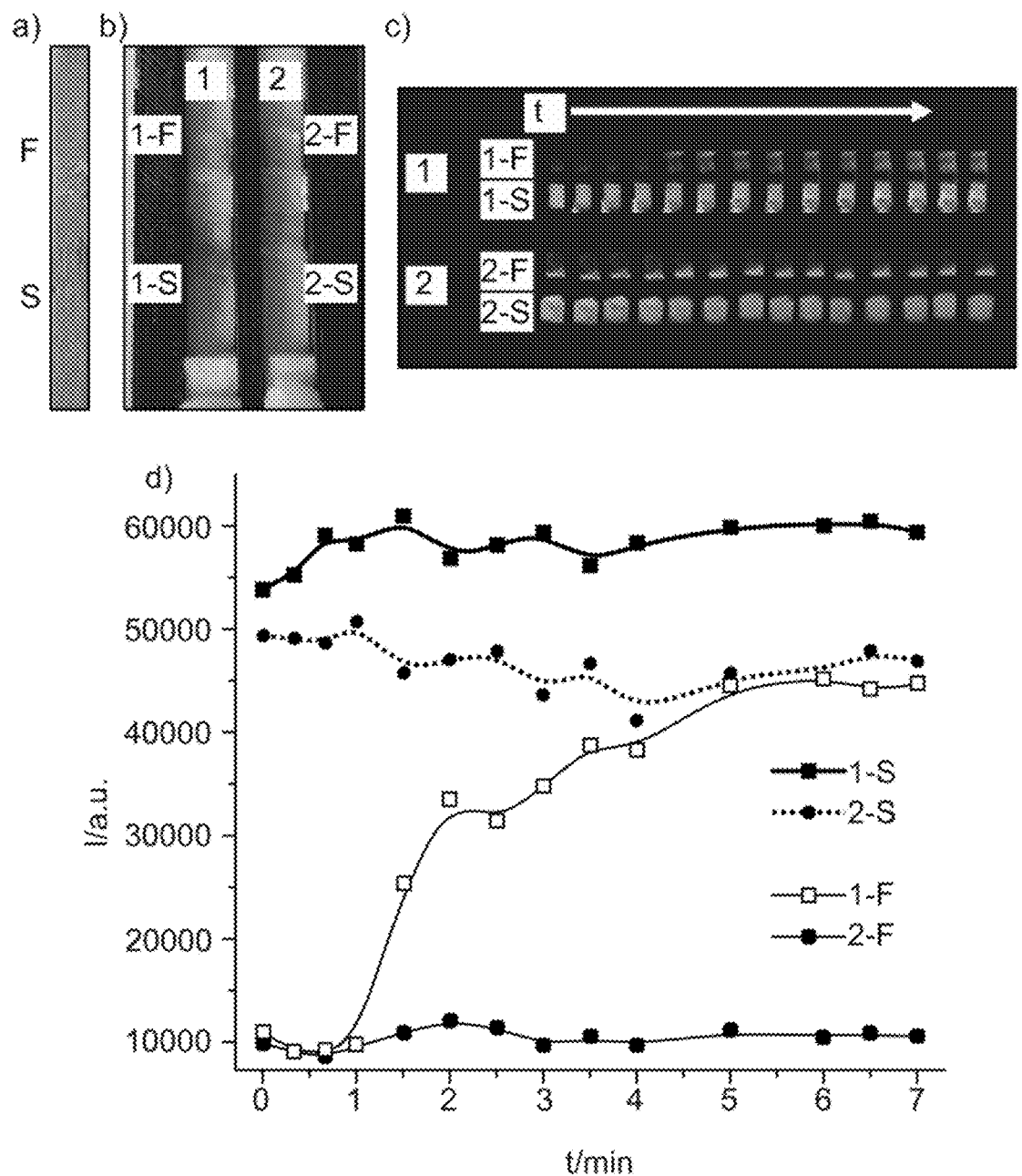
FIG. 7a shows a photograph of the glass fibre strip containing a piece of SURB-M-GF (S) and FLU-M-GF (F) paper as detection zone.
FIG. 7b shows a photograph of the corresponding strips after the flow in absence (2) and in presence (1) of 1 μL of a mixture of FLU and SURB (1 mM) at the bottom of the strips containing a piece of SURB-M-GF (1-S and 2-S) and FLU-M-GF (1-F and 2-F) paper as detection zone.
FIG. 7c shows corresponding photograph of the strips under fluorescence light ($\lambda_{exc}$ 470 nm and $\lambda_{exc}$ 505 nm for excitation, 532 nm cut-off and 550 nm long-pass as filters in emission) as a function of time.
FIG. 7d shows corresponding integrated fluorescence intensities of the area of the detection zones as a function of time evaluated using ImageJ software for the two different capture materials.

In a second experiment, we prepared strips containing two detection zones, a first zone with SURB-M-GF and a second with FLU-M-GF imprinted gels as is depicted in FIG. 7a. On one of the strips, 1 µL of a solution containing a mixture of 1 mM (in total) of FLU and SURB was spotted at ca. 1 cm from the bottom, whereas only solvent was spotted on the other strip, to assess the influence of the solvent alone on the fluorescence. The strips were left in a lateral flow cassette and a piece of glass fibre paper was added at the beginning and at the end to have a sample and an adsorbent pad. 200 µL of PBS were introduced on the sample pad and the flow was monitored using a fluorescence home-made lamp as described before. FIGS. 7b) and 7c) show the colour and fluorescence observed at the corresponding zones as a function of time (6c) and at the end of the experiment (6b). As can be seen, SURB was only retained in the SURB-M-GF zone (S), whereas FLU was retained only in the FLU-M-GF zone (F). FIG. 7d shows the amount of fluorescence retained as a function of time on the strips as quantified by ImageJ. As can be seen, in the absence of the dyes no changes of the background were observed for FLU-M-GF strips (2F), whereas a small decrease of the background was observed for SURB-M-GF, ascribed to the transition of dry to wet state of the gel (2S). In presence of the mixture of dyes, an increase of the fluorescence was observed first on the first zone, ascribed to SURB-M-GF (1S), whereas after 2 min, an increase of the fluorescence was also observed in the second FLU-M-GF zone, due to retention of FLU (2S).

In the following, studies employing gated sensing materials in the interaction zone, i.e. in the sensing zone, will be described. Encouraged by the results found with the fluorescent dyes in the model studies, we decided to also use the gated sensing materials on strip. For that purpose, glass fibre paper was used as a porous matrix. We spotted 2 µL of a 5 mg mL$^{-1}$ suspension of a sensing material which is able to specifically detect pentaerythritol tetranitrate (PETN) and which contains SURB inside of the pores.

Figure 8:
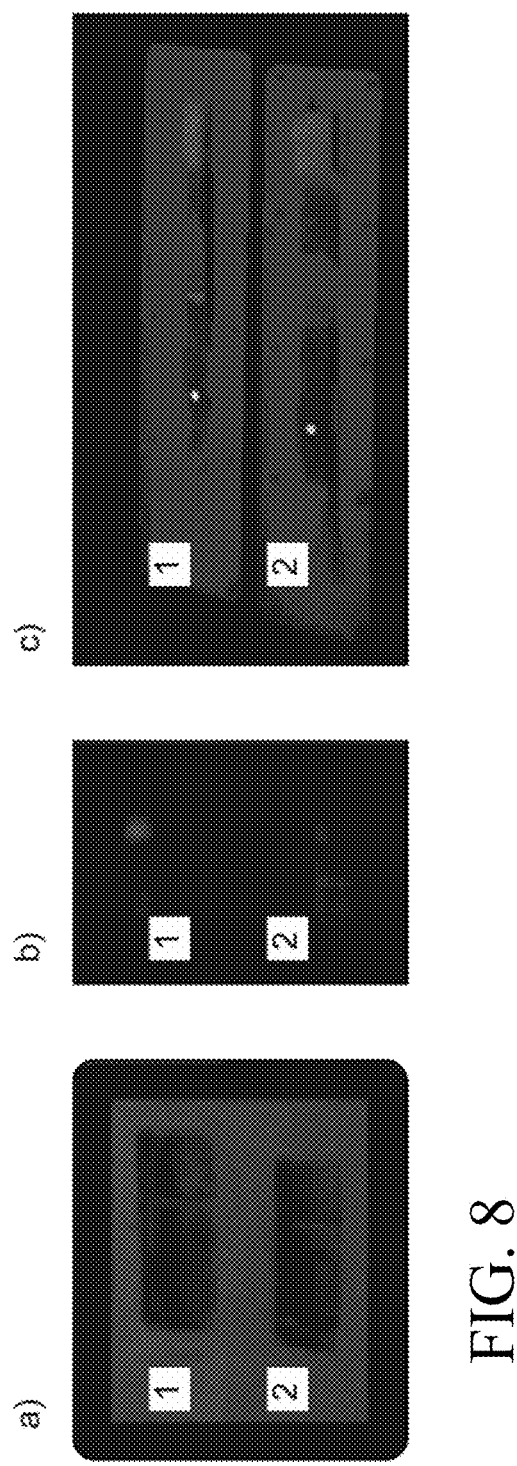
FIG. 8a shows a test strip adapted for a lateral flow assay containing a PDDAC line (17%, 6 mm) as capture material and a sensing material able to detect PETN in the reporter release zone 2) after flow in presence (1) and in absence (2) of PETN (25 ppm) using 80 mM PBS containing 2.5% MeOH as solvent. Therein PETN stands for the model analyte pentaerythritol tetranitrate.
FIG. 8b comprises the corresponding assay but using a PDDAC line (35%, 3 mm) instead of (17%, 6 mm) as capture zone
FIG. 8c shows the corresponding assay using a line of PDDAC (applied as a 35% solution at a line width of 6 mm) as capture zone.
Figure 9:
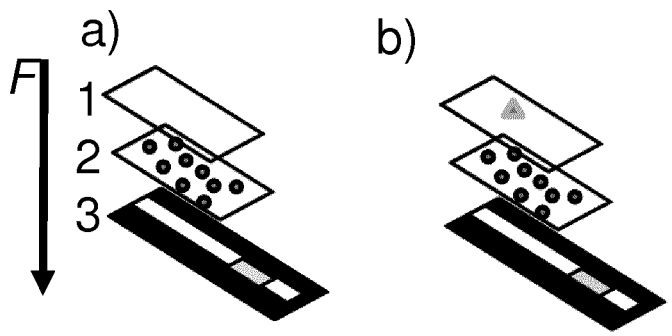
FIG. 9 shows the working principle of a stacked lateral flow assay containing the different zones stacked vertically. The sample injection zone 1 is arranged atop and the reporter release zone 2 is located in a second layer of paper. As a third layer, a strip containing the detection zone 3 is arranged at the bottom. During the vertical flow F, the reporter (e.g. optical reporter molecules) encapsulated in the sensing material of the reporter release zone 2 are released only when the respective analyte is present in a sample b and then move with the flow by capillary forces toward the capture zone 3, where it is retained for detection. In the absence of analyte in a sample (as shown in a), no release is registered, whereas in case (designated as b) the analyte from the sample may be detected in the detection zone.
Figure 10:
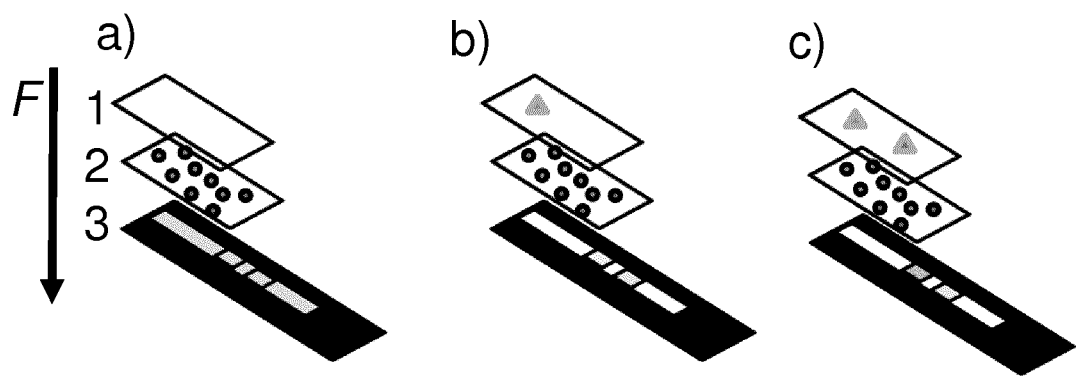
FIG. 10 illustrates schematically the working principle of a stacked lateral flow assay for the case of the detection of multiple analytes. Different porous matrix layers placed atop each other comprise the sample injection zone (1), and a reporter release zone containing a mixture of e.g. two sensing particles containing two different reporter molecules, which are adapted to selectively interact with two different analytes. The stack comprises also a layer of porous matrix comprising a structured detection zone 3. The bottom layer with the two different detection zones comprises a channel pattern which may be generated, e.g., by a wax print. There two different detection zones with two different capture materials which are selective for the corresponding reporter molecules are shown. During the flow F, the corresponding reporter molecules are released from the reporter release zone only when the respective analyte is present in the applied above sample (b-c) and then move with the flow by capillary forces toward the capture zones 3, where they are retained for detection. In the absence of analyte in a sample (as shown in part a) of this scheme), no release is registered and none of the detection zones generates a signal. Different reporter release zones may also be applied in different matrix layers stacked atop the matrix layer comprising the detection zones. At the end of the channel formed in the bottom layer an absorbing pad may be arranged. The layer comprising the detection zone(s) may be accessible for optical detection means from above or from below.

In a first experiment, different strips were prepared using PDDAC solutions of 17 and 35%. We prepared several strips containing a line of 6 mm of PDDAC (17%) as a detection zone and others containing lines of 3 or 6 mm of a 35%-solution as detection zones. The strips were developed with flowing 160 µL PBS (80 mM, containing 2.5% MeOH) spiked with either 25 ppm PETN or containing no analyte. FIG. 8 shows that only in the presence of PETN, a considerable amount of dye could be detected in the capture zone (Line 1, FIG. 8). Furthermore, with a diluted polymer line (17%, FIG. 8a) the dye was less concentrated in comparison to the line with 35% PDDAC (FIG. 8b for 3 mm band and FIG. 8c for 6 mm band). Despite the results found, the retention of the dye in cases a) and b) was only effective until the first 4 min have passed, the dye not being retained anymore after that time. An effective retention was only observed by the 35%-solution and a broad band of 6 mm, which stopped the flow of the dye across the polymer line. This setup was retaining the dye for more than 30 min.

In contrast to the presented examples and embodiments, known lateral flow assays are based on the traditional reporter approach and no amplification of the signal is produced. The signal on the "test line" and "control line" of the traditional lateral flow tests is generated due to the direct reaction of the analyte (which in a previous step is able to react with the corresponding antibody coupled to coloured or fluorescent particles) with the corresponding antibody covalently bound on the strip, having an stoichiometry of 1:1. According to the embodiments described herein, advantageously a massive signal amplification can be obtained, first, by applying the sensitive material present in the reporter release zone, and second, by the capture and focusing of the selectively released reporter in the detection zone.

Whereas in most of the previously known lateral flow assays the detection of the analyte requires the presence of a second binding agent as a reporter, the embodiments described herein are label-free. Advantageously, according to one or several of the described embodiments more than one analyte per channel can be detected and quantified. Controlled focusing or concentration for released reporter molecules in specific capture zones has not been demonstrated previously.

According to embodiments presented therein, the porous matrix of the lateral flow strips can comprise:

a) Cellulose, cotton, cloth, graphene, carbon nanotubes (CNT); glass fibre paper, glass or polymers modified with certain organic groups able to interact specifically with the optical reporter.

b) Certain molecular imprinted polymers (MIPs) or imprinted gels for the specific detection of the optical reporter, cationic or anionic polyelectrolytes, silica or alumina mesoporous materials (for instance $SiO_2$ type MCM- 41, HMS, MSU-n, M5U-V, F5M-16, KSW-2, SBA-n (n=1, 2, 3, 8, 11-16), FDU-n (12, 14, 15, 16), UVM-7, UVM-8, M-UVM-7 or M-UVM-8, A1203 type MCM-41) modified with certain organic groups using several organosilanes (for instance amino groups using 3-aminopropyltriethoxysilane (APTES) or carboxylic acid groups by a ring opening linker elongation reaction of the amino groups with succinic anhydride.

With the employment of materials able to selectively interact with different optical reporter molecules it is possible to create several areas in the detection zone, allowing for spatial concentration of the reporter molecules to improve sensitivity and for the possibility to detect several substances simultaneously on one single strip.

The reported signal is generated in an area that is spatially separated from the interaction of the sensing material with the analyte. The signal reported is thus only based on the capture of the optical reporter molecule released after the interaction of the sensing material with the analyte. No labelling or use of secondary binding agents is necessary to produce a signal in a defined area.

Because the optical reporter molecules are not contained in the samples and the functional groups of the capture zone are always in a high excess with respect to the reporter molecules, complete retention of the reporter molecule in the capture zone can be easily accomplished with rather simple forces such as electrostatic, H-bonding, covalent bond (for instance for the detection of sugars with boronic acids), coordinative, π-π stacking or hydrophobic interaction.

Furthermore, it is possible to use a pattern of capture materials in the detection zone for a mixture of gated materials incorporating different optical reporter molecules, allowing for the simultaneous detection of several analytes with one test strip or stick.

Typical embodiments comprise the use of a capture material in a designated zone that does not interact with the analyte or a labelled competitor, but that can take up and retain a chemically entirely different optical reporter molecules at much higher concentration than the analyte. That allows a focused amplified detection of an analyte and its semi-quantitative analysis.

Advantageously, multiple or structured detection zones on lateral flow strips, planar substrates or sticks for multiplexed optical detection can be created.

Advantageously, the detection of analytes according to one or a combination of the described embodiments is label-free.

Furthermore, an increase in sensitivity is achieved, not only because of the described signal amplification generated by the sensing material employed, but because of dedicated capture and concentration of the released reporter molecules.

Some aspects of the embodiments described herein can be summarized as follows.

1. Suggested is the design of a test strip or a dip stick which is adapted for a lateral flow assay (see FIG. 1) and which comprises:
a) a section or segment for sample introduction; b) a section or segment containing a mesoporous hybrid sensing material able to specifically interact with the analyte; and c) a section or segment containing the capture material, the capture material being able to interact with the optical reporter molecule(s), the reporter molecule(s) being released from the mesoporous hybrid sensing material.

2. A test strip as described in aspect 1, in which the sensing material comprises a porous support material having pores and an optical reporter molecule which is contained in the pores of the porous support material, wherein the pores of the porous support material are closed by a pore-closing material forming non-covalent bonds with the porous support material, wherein the pore-closing material is selected to specifically bind an analyte in a liquid sample, and wherein the optical reporter molecule is released from unclosed pores, when the analyte specifically binds to the pore closing material.

3. A test strip as described in aspect 1, wherein the material able to interact with the optical reporter molecule is a modified cellulose or glass fibre paper with certain organic groups able to interact with said reporter. The organic groups are selected, e.g., from amino groups or carboxylic acid groups.

4. A test strip as described in aspect 1, wherein the material able to interact with the optical reporter molecule is a modified mesoporous material with certain organic groups able to interact with said reporter. Organic groups are able to be adsorbed or covalently bound to the surface.

5. A test strip as described in aspect 1, wherein the material able to interact with the optical reporter molecule is a molecularly imprinted polymer generated against said reporter and able to interact specifically with it.

6. A test strip as described in aspect 1, wherein the material able to interact with the optical reporter molecule is an imprinted gel able to interact specifically with said reporter.

7. A test strip as described in aspect 1, wherein the material able to interact with the optical reporter molecule is a nitrocellulose or glass fibre paper containing directly grafted a molecularly imprinted polymer or an imprinted gel able to interact specifically with said reporter.

8. A test strip as described in aspect 1, wherein the section or segment containing the mesoporous sensing material comprises a pattern of different mesoporous sensing materials (see FIG. 4).

9. A test strip as described in aspect 1, wherein the section containing the material described in aspects 3-7 contains an ordered pattern or array of materials described in claims 3-7, with the aim to detect simultaneously the presence of more than one analyte (see FIG. 4).

10. A sensing material as described in aspect 2, wherein the optical reporter is described in the following table 1.

11. A test strip as described in aspect 1, wherein the combinations of capture materials and optical reporter molecules are described in the following Table 2.

TABLE 1

Classes of optical reporter molecules.

| Class | Optical reporter molecules |
|---|---|
| #1 | Rhodamine and derivatives |
| | Fluorescein and derivatives |
| | Styryl derivatives |
| | Cyanine and polymethine derivatives |
| | Pyridinium derivatives |
| | Pyrylium and thiopyrylium derivatives |
| | Ruthenium, osmium or iridium complexes and derivatives |
| | Luminescent complexes of rare earth elements (such as europium or terbium) |
| | Squarylium and derivatives |
| #2 | Coumarin and derivatives |
| | Dipyrromethene or BODIPY and derivatives |
| | Pyrromethane and derivatives |
| | Benzofuran and derivatives |
| | Pyridine derivatives |
| | Naphthalimide and derivatives |

TABLE 1-continued

Classes of optical reporter molecules.

| Class | Optical reporter molecules |
|---|---|
| | Benzoxazole and derivatives |
| | Benzoxadiazole and derivatives |
| | Benzindole and derivatives |
| | DAPI and derivatives |
| | Stilbene and derivatives |
| | Oxazine and derivatives |
| | Perylene and derivatives |
| | Azulene and derivatives |
| | Styryl base derivatives |
| | Phycoerythrin and derivatives |
| | Squaraine and derivatives |
| | Porphyrine and derivatives |
| | Phthalocyanine and derivatives |
| #3 | Cationic and anionic derivatives of all the dyes in #2. |

TABLE 2

Combinations of capture materials and optical reporter molecules of Table 1.

| Capture materials | Optical reporter molecules |
|---|---|
| Cellulose paper, glass fibre paper, cotton paper, glass, silica or alumina mesoporous materials (e.g. SiO$_2$-type MCM-41, HMS, MSU-n, MSU-V, FSM-16, KSW-2, SBA-n (n = 1, 2, 3, 8, 11-16), UVM-7, UVM-8, M-UVM-7 or M-UVM-8, Al$_2$O$_3$-type MCM-41) containing amino or carboxylic acid groups covalently bound at the surface. | Class #1 and #3 of Table 1 |
| Cellulose paper, glass fibre paper, cotton paper, glass, silica or alumina mesoporous materials (e.g. SiO$_2$-type MCM-41, HMS, MSU-n, MSU-V, FSM-16, KSW-2, SBA-n (n = 1, 2, 3, 8, 11-16), UVM-7, UVM-8, M-UVM-7 or M-UVM-8, Al$_2$O$_3$-type MCM-41) containing amino or carboxylic acid groups covalently bound at the surface and polyelectrolytes adsorbed at the surface. | Class #1 and #3 of Table 1 |
| Molecular imprinted gels (MIG) | Class #1, #2 and #3 of Table 1 |
| Molecular imprinted polymers (MIP) using optical reporter molecules of column 2 | Class #1, #2 and #3 of Table 1 |
| Core-MIP shell particles (core = silica or polymer) | Class #1, #2 and #3 of Table 1 |
| Cellulose paper, glass fibre paper, cotton paper, glass containing molecular imprinted gels or core-MIP shell particles | Class #1, #2 and #3 of Table 1 |

ABBREVIATIONS

MCM-41, HMS, MSU-n, MSU-V, FSM-16, KSW-2, SBA-n (n=1, 2, 3, 8, 11-16), UVM-7, FDU-n (12, 14, 15, 16), UVM-8, M-UVM-7 or M-UVM-8, Al2O3-type MCM-41=mesoporous materials
AAm=acrylamide
APS=ammoniumpersulfate
APTES=3-aminopropyltriethoxysilane
APTES-C=APTES-modified cellulose paper
APTES-GF=APTES-modified glass fibre paper
APTES-MCM=APTES-modified MCM-41
APTES-SBA=APTES-modified SBA-15
CTAB=n-cetyltrimethylammonium bromide
COOH-MCM=COOH-modified MCM-41
COOH-C=COOH-modified cellulose paper
COOH-GF=COOH-modified glass fibre paper
COOH-SBA=COOH-modified SBA-15
EBAAm=N,N'-ethylene bis(acrylamide
FLU=2,7-dichlorofluorescein
FLU-M-GF=2,7-dichlorofluorescein modified M-GF
FLU-MIG=2,7-dichlorfluorescein modified molecular imprinted gel
M=3-(trimethoxysilyl)propyl methacrylate
M-GF=3-(trimethoxysilyl)propyl methacrylate modified glass fibre paper=methacrylate-glass fibre paper
MCM=mesoporous material, MCM-41
MeCN=acetonitrile
MeOH=methanol
MIG=molecular imprinted gel
NIG=non imprinted gel
NIG-M-GF=non imprinted gel-modified M-GF
NIPAAm=N-isopropylacrylamide
P123=EO$_{20}$-PO$_{70}$-EO$_{20}$=triblock poly(ethylene oxide)-poly(propylene oxide)-poly(ethylene oxide)
PA-COOH-MCM=PDDAC-modifiedCOOH-MCM-41
PBS=Phosphate buffered saline
PDDAC=poly(diallyldimethylammonium chloride)
PETN=pentaerythritol tetranitrate
PVP=Poly(vinylpyrrolidone)
PVP-APTES-MCM=PVP-modified APTES-MCM-41
R6G=rhodamine 6G
R6G-M-GF=rhodamine 6G imprinted polymer on glass fibre paper
R6G-MIG=rhodamine 6G molecular imprinted gel
RuBipy=Ruthenium bipyridine
RuBipy-M-GF=Rubidium bipyridine imprinted gel on glass fibre paper
RuBipy-MIG=Rubidium bipyridine imprinted gel
SBA-15=mesoporous silica material (Santa Barbara Amorphous),
SURB=sulforhodamine B
SURB-M-GF=sulforhodamine B modified M-GF
SURB-MIG=sulforhodamine B modified molecular imprinted gel
SURG=sulforhodamine G
SURG-M-GF=sulforhodamine G modified M-GF
SURG-MIG=sulforhodamine G modified MIG
TEMED=N,N,N',N'-tetramethylethylenediamine
TEOS=tetraethylorthosilicate;

Aspects of the application can be summarized as listed below:
1. A test strip comprising a porous matrix, the test strip comprising:
   a sample application zone for applying a liquid sample comprising an analyte;
   a reporter release zone, comprising a sensing material, the sensing material being adapted to selectively interact with the analyte by releasing an optical reporter, the reporter release zone being arranged downstream of the sample application zone;
   a detection zone, comprising a capture material, the capture material being adapted to selectively bind the optical reporter and being arranged downstream of the reporter release zone.
2. The test strip according to aspect 1, wherein the optical reporter is contained in pores of the sensing material, wherein the pores of the sensing material are closed by a pore-closing material, wherein the pore-closing material is selected to specifically bind the analyte, releasing the optical reporter from the pores when the analyte specifically binds to the pore-closing material.

3. The test strip according to aspect 2, wherein the pore-closing material is non-covalently bound to the sensing material, and detaches from the sensing material if bound by the analyte.
4. The test strip according to any of aspects 1 to 3, wherein the optical reporter comprises a fluorescent dye, a colored dye or a luminescent inorganic fluorescent ion of a rare earth element.
5. The test strip according to aspect 4, wherein the fluorescent dye comprises at least one of a rhodamine; a fluorescein; a styryl; a cyanine or polymethine; a pyridinium; a pyrylium; a thiopyrylium; a ruthenium complex; an osmium complex, an iridium complex; a luminescent complex of a rare earth element; a squarylium derivative; a neutral, a cationic or an anionic derivative of coumarin, of dipyrromethene or BODIPY, of pyrromethene, of benzofurane, of pyridine, of naphthalimide, of benzoxazole, of benzoxadiazole, of benzindole, of DAPI, of stilbene, of oxazine, of perylene, of azulene, of a styryl base, of phycoerythrin, of squaraine, of porphyrine, or of a phthalocyanine dye.
6. The test strip according to any of aspects 1 to 5, wherein the capture material is selected from a molecular imprinted polymer, a polyelectrolyte or a functionalized mesoporous material comprising at least one of: a thiol, a isocyanate, an amino-group, an hydroxy-group, an epoxy-group, a carboxylic group or a charged functional group such as quarternary ammonium group.
7. The test strip according to aspect 6, wherein the capture material is selected from a molecular imprinted polymer, the molecular imprinted polymer being generated by polymerization of at least one or more types of a monomer selected from: acrylamide, vinyl pyridine, N-isopropylacrylamide,2-hydroxyethyl methacrylate, methyl methacrylate, benzyl methacrylate, methacrylate, methacrylamide, N,N'-dimethyl methacrylamide, vinylalcohol, vinylimidazole; with a crosslinking agent selected from: ethylene dimethacrylate, ethylene glycol dimethacrylate, poly(acrylic acid), a bis(-hydroxyethyl) sulfone, trimethylolpropane trimethacrylate or pentaerythritol triacrylate.
8. The test strip according to aspect 6, wherein the capture material is selected from a polyelectrolyte, wherein the polyelectrolyte typically comprises polycations or polyanions such as for instance poly(diallyldimethylammonium chloride), poly(allylamine) hydrochloride, poly(ethylenimine) (PEI), poly(acrylic acid), poly(vinylpyrrolidone) (PVP), poly(sodium styrene sulfonate) (PSS), a cyclodextran or a polydextran.
9. The test strip according to any of aspects 1 to 8, further comprising an absorption zone, the absorption zone being arranged downstream of the detection zone and adapted to absorb the solvent.
10. The test strip according to any of aspects 1 to 9, wherein an area of the test strip comprising at least one or more detection zones is surrounded by a barrier, the barrier either closing the pores of the porous matrix and/or modifying a wettability of the porous matrix for the solvent and forming a channel in the porous matrix.
11. The test strip according to aspect 10, wherein the barrier is formed by a wax.
12. The test strip according to any of aspects 1 to 11, wherein the sensing material comprises a mesoporous inorganic material.
13. The test strip according to aspect 12, wherein the mesoporous inorganic material comprises silica, alumina, $TiO_2$, carbon, carbonitride, silicon carbide, silicon oxycarbide, silicon carbonitride, silicon nitride, silicon oxynitride, silicon aluminum nitride, or silicoboron carbonitride.
14. The test strip according to any of aspects 1 to 13, wherein the porous matrix is selected from a paper, a felt, a nonwoven, a fibre, a pressed or sintered powder, a cloth, or a tissue, wherein the paper, the felt, the nonwoven, the fibre, the pressed or sintered powder, the cloth, and the tissue comprise at least one of a polymer, a glass, a ceramic, a carbon, a graphene, a mineral, or a metal.
15. The test strip according to any of aspects 1 to 14, wherein the test strip comprises one reporter release zone and between 2 and 7 detection zones.
16. The test strip according to any of aspects 1 to 15, wherein the test strip at least at the reporter release zone and/or at the detection zone comprises at least two matrix layers.
17. The test strip according to any of aspects 1 to 16, wherein a shape of the strip deviates from a non-square rectangle, and comprises at least a section of a circle or of a triangle.
18. The test strip according to any of aspects 1 to 17, wherein the sample application zone is arranged on top of the reporter release zone.
19. A method for detecting an analyte, the method comprising:
    providing a test strip according to any of aspects 1 to 18;
    applying a sample to the sample application zone of the test strip;
    detecting a presence and/or a quantity and/or a concentration of the optical reporter in the at least one detection zone;
    determining a presence and/or a concentration of the analyte in the sample.
20. The method according to aspect 19, further comprising providing a liquid for generating a continuous or discontinuous fluid stream from the sample application zone to the reporter release zone and/or from the reporter release zone to at least one detection zone.
21. The method according to aspect 20, wherein the optical reporter is a fluorescent dye and the detecting is accomplished by a fluorescence measurement with a hand-held device.

The present invention has been explained with reference to various illustrative embodiments and examples. These embodiments and examples are not intended to restrict the scope of the invention, which is defined by the claims and their equivalents. As is apparent to one skilled in the art, the embodiments described herein can be implemented in various ways without departing from the scope of what is invented. Various features, aspects, and functions described in the embodiments can be combined with other embodiments.

The invention claimed is:
1. A test strip comprising a porous matrix, the test strip comprising:
    a sample application zone for applying a liquid sample comprising an analyte;
    a reporter release zone, comprising a sensing material having pores, an optical reporter contained in the pores, and a pore-closing material closing the optical reporter in the pores, the pore-closing material being adapted to selectively interact with the analyte and thereby release the optical reporter, the reporter release zone being arranged downstream of the sample application zone;

a detection zone, comprising a capture material, the capture material being adapted to selectively bind the optical reporter and being arranged downstream of the reporter release zone, wherein the capture material is selected from: a molecular imprinted polymer, a polyelectrolyte, and a functionalized mesoporous material comprising at least one of: a thiol, a isocyanate, an amino-group, a hydroxy-group, an epoxy-group, a carboxylic group or a charged functional group.

2. The test strip according to claim 1, wherein the pore-closing material is non-covalently bound to the sensing material, and detaches from the sensing material if bound by the analyte, and wherein the optical reporter comprises a fluorescent dye, a colored dye or a luminescent inorganic fluorescent ion of a rare earth element.

3. The test strip according to claim 2, wherein the fluorescent dye comprises at least one of a rhodamine; a fluorescein; a styryl; a cyanine or polymethine; a pyridinium; a pyrylium; a thiopyrylium; a ruthenium complex; an osmium complex, an iridium complex; a luminescent complex of a rare earth element; a squarylium derivative; a neutral, a cationic or an anionic derivative of coumarin, of dipyrromethene or BODIPY, of pyrromethene, of benzofurane, of pyridine, of naphthalimide, of benzoxazole, of benzoxadiazole, of benzindole, of DAPI, of stilbene, of oxazine, of perylene, of azulene, of a styryl base, of phycoerythrin, of squaraine, of porphyrine, or of a phthalocyanine dye.

4. The test strip according to claim 1, wherein an area of the test strip comprising at least one or more detection zones is surrounded by a barrier, the barrier either closing the pores of the porous matrix and/or modifying a wettability of the porous matrix for liquid of the liquid sample and forming a channel in the porous matrix.

5. The test strip according to claim 4, wherein the barrier is formed by a wax.

6. The test strip according to claim 1, wherein the sensing material comprises a mesoporous inorganic material, wherein the mesoporous inorganic material comprises silica, alumina, $TiO_2$, carbon, carbonitride, silicon carbide, silicon oxycarbide, silicon carbonitride, silicon nitride, silicon oxynitride, silicon aluminum nitride, or silicoboron carbonitride.

7. The test strip according to claim 1, wherein the porous matrix is selected from a paper, a felt, a nonwoven, a fibre, a pressed or sintered powder, a cloth, or a tissue, wherein the paper, the felt, the nonwoven, the fibre, the pressed or sintered powder, the cloth, and the tissue comprise at least one of a polymer, a glass, a ceramic, a carbon, a graphene, a mineral, or a metal.

8. The test strip according to claim 1, wherein the test strip comprises one reporter release zone and between 2 and 7 detection zones.

9. The test strip according to claim 1, wherein the reporter release zone and/or the detection zone comprises at least two matrix layers.

10. The test strip according to claim 1, wherein a shape of the test strip deviates from a non-square rectangle, and comprises at least a section of a circle or of a triangle.

11. The test strip according to claim 1, wherein the sample application zone is arranged on top of the reporter release zone.

12. A method for detecting an analyte, the method comprising:
providing a test strip according to claim 1;
applying a sample to the sample application zone of the test strip;
detecting a presence and/or a quantity and/or a concentration of the optical
reporter in the at least one detection zone;
determining a presence and/or a concentration of the analyte in the sample.

13. The method according to claim 12, further comprising providing a liquid for generating a continuous or discontinuous fluid stream from the sample application zone to the reporter release zone and/or from the reporter release zone to at least one detection zone.

14. The method according to claim 13, wherein the optical reporter is a fluorescent dye and the detecting is accomplished by a fluorescence measurement with a hand-held device.

15. The test strip according to claim 1, wherein a plurality of the pores of the sensing material contain a plurality of different optical reporters.

16. The test strip according to claim 15, wherein a plurality of different pore-closing materials are bound to the sensing material and are configured to bind to different analytes, and wherein binding of a pore-closing material to an analyte releases a corresponding optical reporter indicating a corresponding analyte.

17. The test strip according to claim 16, wherein the test strip comprises a plurality of detection zones corresponding to the plurality of different optical reporters.

* * * * *